(12) United States Patent　　　　(10) Patent No.: US 12,648,684 B2

Massicotte　　　　　　　　　　　　(45) Date of Patent: Jun. 9, 2026

(54) DRIVE TRAINS FOR TOROIDAL VEHICLES POWERED BY DIRECT-CURRENT MOTORS

(71) Applicant: J. Mathieu Massicotte, North Reading, MA (US)

(72) Inventor: J. Mathieu Massicotte, North Reading, MA (US)

( * ) Notice: Subject to any disclaimer, the term of this patent is extended or adjusted under 35 U.S.C. 154(b) by 196 days.

(21) Appl. No.: 18/416,071

(22) Filed: Jan. 18, 2024

(65) Prior Publication Data

US 2024/0237877 A1　　Jul. 18, 2024

Related U.S. Application Data

(60) Provisional application No. 63/439,620, filed on Jan. 18, 2023.

(51) Int. Cl.
| | |
|---|---|
| *A61B 1/00* | (2006.01) |
| *A61B 1/05* | (2006.01) |
| *A61B 5/06* | (2006.01) |

(52) U.S. Cl.
CPC ...... *A61B 1/00156* (2013.01); *A61B 1/00016* (2013.01); *A61B 1/00032* (2013.01); *A61B 1/00082* (2013.01); *A61B 1/00142* (2013.01); *A61B 1/00148* (2022.02); *A61B 1/0016* (2013.01); *A61B 1/05* (2013.01); *A61B 5/06* (2013.01)

(58) Field of Classification Search
CPC ............ A61B 1/00011; A61B 1/00025; A61B 1/00082; A61B 1/00142; A61B 1/041; A61B 1/05; A61B 1/00156; A61B 1/0016; A61B 1/008
See application file for complete search history.

(56) References Cited

U.S. PATENT DOCUMENTS

| | | | |
|---|---|---|---|
| 6,971,990 B2 | 12/2005 | Ziegler et al. | |
| 8,343,170 B2 | 1/2013 | Massicotte | |
| 8,529,581 B2 | 9/2013 | Massicotte | |
| 9,693,676 B2 | 7/2017 | Massicotte | |
| 10,213,208 B2 | 2/2019 | Massicotte | |
| 11,413,435 B2 | 8/2022 | Massicotte | |
| 2002/0117097 A1* | 8/2002 | Dong | B63H 5/14 |
| | | | 114/67 R |
| 2004/0204702 A1* | 10/2004 | Ziegler | A61B 1/04 |
| | | | 606/1 |

(Continued)

*Primary Examiner* — Aaron B Fairchild

(74) *Attorney, Agent, or Firm* — Gesmer Updegrove LLP

(57) ABSTRACT

A device fashioned in the shape of a toroid is rotated by an internal mechanism that propels itself in one or more directions based on internal rotation of the toroidal tread. In one specific example, the tread of the vehicle is self-contained and the vehicle's entire outer surface is dynamic. Such a device is uniquely and ideally suitable for exploration of a tubular structure such as, but not limited to, the alimentary tract. Because of its small size, the toroidal device is propelled by a fast-spinning DC motor that requires a novel drivetrain to spin the device's toroidal tread. The novelties described herein are related to the unique geometry and rotation of the tread in a toroidal vehicle, the configuration of a toroidal vehicle that requires that the axle of the motor to spin perpendicularly to the axis of it wheels, and the small size of internal components necessary to fit within the internal space of the toroidal tread and the overall small size of the toroidal vehicle.

27 Claims, 20 Drawing Sheets

(56)                    References Cited

U.S. PATENT DOCUMENTS

| | | | |
|---|---|---|---|
| 2006/0070775 A1 * | 4/2006 | Anhalt .................. | B62D 57/00 |
| | | | 180/9.1 |
| 2011/0065988 A1 * | 3/2011 | Eidenschink .......... | A61B 1/267 |
| | | | 600/115 |
| 2011/0265275 A1 * | 11/2011 | Allen ................. | A61B 1/00156 |
| | | | 15/104.05 |
| 2012/0029283 A1 * | 2/2012 | Yamakawa ........ | A61B 1/00156 |
| | | | 600/114 |
| 2013/0261391 A1 * | 10/2013 | Dejima ............. | A61B 1/00156 |
| | | | 600/114 |
| 2014/0336455 A1 * | 11/2014 | Massicotte ......... | A61B 1/00156 |
| | | | 600/109 |
| 2018/0008130 A1 * | 1/2018 | Holzer .................... | A61B 1/31 |

* cited by examiner 1a          1b          1c                    1d

Motor's Axle

Wheel's Axle

Axle

Coreless
DC motor

Planetary
Stepdown
Gearbox

Bevel Gear

Hypoid Gear

Worm Gear

FIG. 6C

DRIVE TRAINS FOR TOROIDAL VEHICLES POWERED BY DIRECT-CURRENT MOTORS

CROSS-REFERENCE TO RELATED APPLICATIONS

This application claims the benefit of U.S. Provisional Application No. 63/439,620, filed Jan. 18, 2023, which is hereby incorporated herein by reference in its entirety.

TECHNICAL FIELD

The present invention relates generally to medical devices. More specifically, the present invention is related to toroidal vehicles and drive trains for such toroidal vehicles that are powered by direct current (DC) motors.

BACKGROUND OF THE INVENTION

The toroidal tread-driven vehicle was introduced by J. Mathieu Massicotte in U.S. Pat. No. 9,693,676 entitled 'Toroidal balloon-driven vehicle.' It is a novel device whose locomotion depends upon a toroidal tread. The entire external surface of a toroidal vehicle is the tread, allowing it to traverse challenging environments such as the intestines.

A drive train for such a vehicle is hard since there is no separate prior art to describe potential drivetrains in a toroidal vehicle. Within the rotating toroidal tread is a protected cylindrical space for the vehicle's internal components, including but not limited to a motor, a drivetrain, a power source, and electronics. Not only is this toroidal device unique, it has dimensional characteristics that necessitate the development of unique configurations and mechanisms for its function.

For example, the device is so small that only a few options for a DC motor exist. Furthermore, the small motor drives internal wheels whose axles are perpendicular to the axles of the rotating motors.

As a result, a novel drivetrain is necessary to translate the spinning of the motor to the spinning of the wheels. Motors of this small size spin at very high rates, so the drivetrain must contain step-down gear systems to transform the high-speed motor to a much lower rotational speed appropriate for the movement of the entire toroidal vehicle. And lastly, the mechanical components need to be sufficiently small to function in the very small space inside the rotating tread of this small toroidal vehicle.

This application describes configurational options for the motor and drivetrain for a toroidal vehicle.

SUMMARY OF THE INVENTION

In one embodiment, the present invention provides a device comprising: a toroidal device having a top portion and a bottom portion that are symmetric about a central axis, the top portion having a top inner device surface and a top outer device surface and the bottom portion having a bottom inner device surface and a bottom outer device surface, each of the top inner device surface and top outer device surface having a top inner wall and a top outer wall and each of the bottom inner device surface and bottom outer device surface comprising a bottom inner wall and a bottom outer wall, where a portion of the top outer wall associated with the top inner device surface and another portion of the bottom outer wall associated with the bottom inner device surface are adjacent to each other and are configured to form a channel; (a) the top portion comprising the following components enclosed within the top inner wall: (i) a top geared wheel; (ii) a top internal curved spiral (ICS) gear configured to engage the top geared wheel; (iii) a top internal spur (IS) gear coupled to the top ICS gear; (iv) a top direct current (DC) motor having a top spur gear at one end that is configured to engage the top IS gear and an engagement mechanism at another, opposite end that is configured to engage a top non-geared wheel; and (b) the bottom portion comprising the following components enclosed within the bottom inner wall: (i) a bottom geared wheel; (ii) a bottom ICS gear configured to engage the bottom geared wheel; (iii) a bottom IS gear coupled to the bottom ICS gear; (iv) a bottom DC motor having a bottom spur gear at one end that is configured to engage the bottom IS gear and another engagement mechanism at another, opposite end that is configured to engage a bottom non-geared wheel; the top ICS gear and the bottom ICS gear are part of a single ICS gear confined within the toroidal device and the top IS gear and bottom IS gear are part of a single IS gear within the toroidal device; the top DC motor and the bottom DC motors powered by at least one power source located within the toroidal device; and the top DC motor configured to rotate the top spur gear that engages the top IS gear coupled to the top ICS gear to cause the top geared wheel to move rotationally in a first direction, resulting in a first inversion of the top inner device surface and the top outer device surface and, at the same time, the bottom DC motor configured to rotate the bottom spur gear that engages the bottom IS gear coupled to the bottom ICS gear to cause the bottom geared wheel to move rotationally in a second direction, resulting in a second inversion of the bottom inner device surface and the bottom outer device surface, the first direction opposite that of the second direction, the first and second inversions safely propelling the device without sliding of the top and bottom outer device surfaces against any contacted external wall and allowing low friction movement of the device.

In another embodiment, the present invention provides a device comprising: a toroidal device having a top portion and a bottom portion that are symmetric about a central axis, the top portion having a top inner device surface and a top outer device surface and the bottom portion having a bottom inner device surface and a bottom outer device surface, each of the top inner device surface and top outer device surface having a top inner wall and a top outer wall and each of the bottom inner device surface and bottom outer device surface comprising a bottom inner wall and a bottom outer wall, where a portion of the top outer wall associated with the top inner device surface and another portion of the bottom outer wall associated with the bottom inner device surface are adjacent to each other and are configured to form a channel; (a) the top portion comprising the following components enclosed within the top inner wall: (i) a first top geared wheel; (ii) a second top geared wheel; (iii) a first top internal curved spiral (ICS) gear configured to engage the first top geared wheel; (iv) a first top internal spur (IS) gear coupled to the first top ICS gear; (v) a first top DC motor having a first top spur gear at one end that is configured to engage the first top IS gear; (vi) a second top DC motor that abuts the first top DC motor at one end and having a second top spur gear at another end; (vii) a second top IS gear configured to engage the second top spur gear; and (viii) a second top ICS gear coupled to the second top IS gear and configured to engage the second top geared wheel; and (b) the bottom portion comprising the following components enclosed within the bottom inner wall: (i) a first bottom geared wheel; (ii) a second bottom geared wheel; (iii) a first bottom ICS gear configured to engage the first bottom geared wheel; (iv) a first bottom IS gear coupled to the first bottom ICS gear; (v) a first bottom DC motor having a first bottom spur gear at one end that is configured to engage the first bottom IS gear; (vi) a second bottom DC motor that abuts the first bottom DC motor at one end and having a second bottom spur gear at another end; (vii) a second bottom IS gear configured to engage the second bottom spur gear; and (viii) a second bottom ICS gear coupled to the second bottom IS gear and configured to engage the second bottom geared wheel; the first top ICS gear and the first bottom ICS gear are part of a single first ICS gear confined within the toroidal device and the first top IS gear and first bottom IS gear are part of a single first IS gear within the toroidal device; the second top ICS gear and the second bottom ICS gear are part of a single second ICS gear confined within the toroidal device and the second top IS gear and second bottom IS gear are part of a single second IS gear within the toroidal device; the first top DC motor, the second top DC motor, the first bottom DC motor, and the second bottom DC motor powered by at least one power source located within the toroidal device; and the first top DC motor configured to rotate the first top spur gear that engages the first top IS gear coupled to the first top ICS gear to cause the first top geared wheel to move rotationally in a first direction, and the second top DC motor configured to rotate the second top spur gear that engages the second top IS gear coupled to the second top ICS gear to cause the second top geared wheel to move rotationally in the first direction, resulting in a first inversion of the top inner device surface and the top outer device surface and, at the same time, the first bottom DC motor configured to rotate the first bottom spur gear that engages the first bottom IS gear coupled to the first bottom ICS gear to cause the first bottom geared wheel to move rotationally in a second direction, and the second bottom DC motor configured to rotate the second bottom spur gear that engages the second bottom IS gear coupled to the second bottom ICS gear to cause the second bottom geared wheel to move rotationally in the second direction, resulting in a second inversion of the bottom inner device surface and the bottom outer device surface, the first direction opposite that of the second direction, the first and second inversions safely propelling the device without sliding of the top and bottom outer device surfaces against any contacted external wall and allowing low friction movement of the device.

In yet another embodiment, the present invention provides a device comprising: a toroidal device having a top portion and a bottom portion that are symmetric about a central axis, the top portion having a top inner device surface and a top outer device surface and the bottom portion having a bottom inner device surface and a bottom outer device surface, each of the top inner device surface and top outer device surface having a top inner wall and a top outer wall and each of the bottom inner device surface and bottom outer device surface comprising a bottom inner wall and a bottom outer wall, where a portion of the top outer wall associated with the top inner device surface and another portion of the bottom outer wall associated with the bottom inner device surface are adjacent to each other and are configured to form a channel; (a) the top portion comprising the following components enclosed within the top inner wall: (i) a first top geared wheel; (ii) a second top geared wheel; (iii) a first top internal curved spiral (ICS) gear configured to engage the first top geared wheel; (iv) a second top ICS gear configured to engage the second top geared wheel; (v) a first top internal spur (IS) gear coupled to the first top ICS gear; (vi) a second top IS gear coupled to the second top ICS gear; (vii) a top DC motor having a first top spur gear at one end and a second top spur gear at another, opposite end, the first top spur gear configured to engage the first top IS gear and the second top spur gear configured to engage the second top IS gear; and (b) the bottom portion comprising the following components enclosed within the bottom inner wall: (i) a first bottom geared wheel; (ii) a second bottom geared wheel; (iii) a first bottom ICS gear configured to engage the first bottom geared wheel; (iv) a second bottom ICS gear configured to engage the second bottom geared wheel; (v) a first bottom IS gear coupled to the first bottom ICS gear; (vi) a second bottom IS gear coupled to the second bottom ICS gear; (vii) a bottom DC motor having a first bottom spur gear at one end and a second bottom spur gear at another, opposite end, the first bottom spur gear configured to engage the first bottom IS gear and the second bottom spur gear configured to engage the second bottom IS gear; the first top ICS gear and the first bottom ICS gear are part of a single first ICS gear confined within the toroidal device and the first top IS gear and first bottom IS gear are part of a single first IS gear within the toroidal device; the second top ICS gear and the second bottom ICS gear are part of a single second ICS gear confined within the toroidal device and the second top IS gear and second bottom IS gear are part of a single second IS gear within the toroidal device; the top DC motor and the bottom DC motors powered by at least one power source located within the toroidal device; and the top DC motor configured to rotate the first top spur gear that engages the first top IS gear coupled to the first top ICS gear to cause the first top geared wheel to move rotationally in a first direction, and the top DC motor configured to rotate the second top spur gear that engages the second top IS gear coupled to the second top ICS gear to cause the second top geared wheel to move rotationally in the first direction, resulting in a first inversion of the top inner device surface and the top outer device surface and, at the same time, the bottom DC motor configured to rotate the first bottom spur gear that engages the first bottom IS gear coupled to the first bottom ICS gear to cause the first bottom geared wheel to move rotationally in a second direction, and the bottom DC motor configured to rotate the second bottom spur gear that engages the second bottom IS gear coupled to the second bottom ICS gear to cause the second bottom geared wheel to move rotationally in the second direction, resulting in a second inversion of the bottom inner device surface and the bottom outer device surface, the first direction opposite that of the second direction, the first and second inversions safely propelling the device without sliding of the top and bottom outer device surfaces against any contacted external wall and allowing low friction movement of the device.

The present invention provides electrically driven devices for travel to remote areas within the body. For example, a toroidal vehicle of the present invention may be used to access the intestines for both diagnostic and therapeutic purposes and for guiding separate medical devices to remote locations within the body. The specific device is a drone with a toroidal tread driven by an electric motor. This invention describes drivetrains that connect the vehicle's motor(s) to the rotating wheels. The configurations described here are not limited to toroidal vehicles for use exclusively in the intestines but may also be applied to toroidal devices used for other indications.

BRIEF DESCRIPTION OF FIGURES

The present disclosure, in accordance with one or more various examples, is described in detail with reference to the following figures. The drawings are provided for purposes of illustration only and merely depict examples of the disclosure. These drawings are provided to facilitate the reader's understanding of the disclosure and should not be considered limiting of the breadth, scope, or applicability of the disclosure. It should be noted that for clarity and ease of illustration these drawings are not necessarily made to scale.

Figure 1:
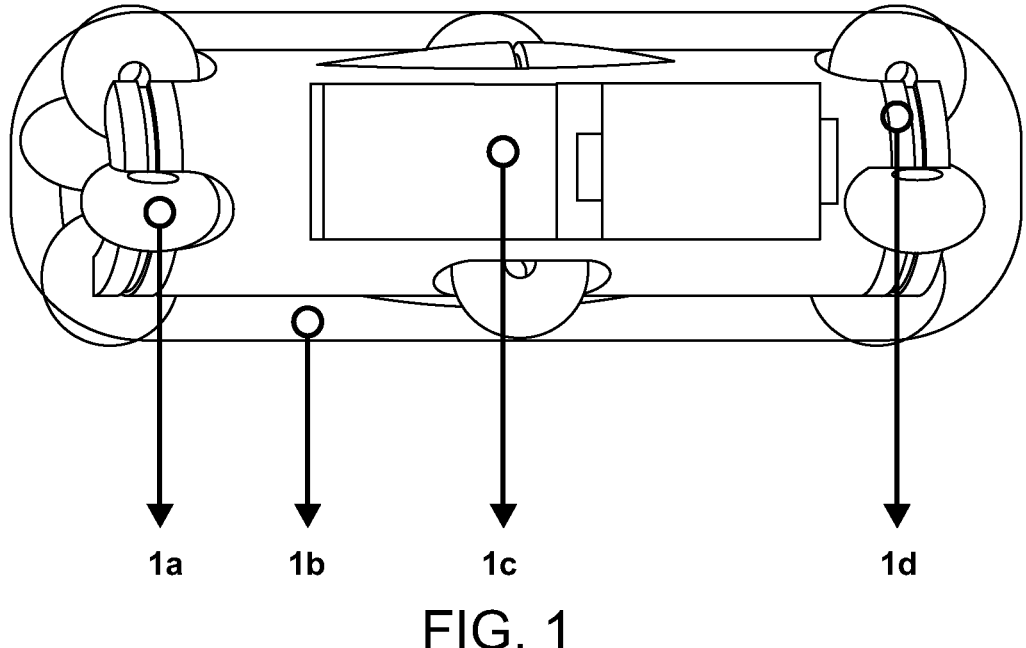

FIG. 1 shows an example of a toroidal vehicle.

Figure 2:
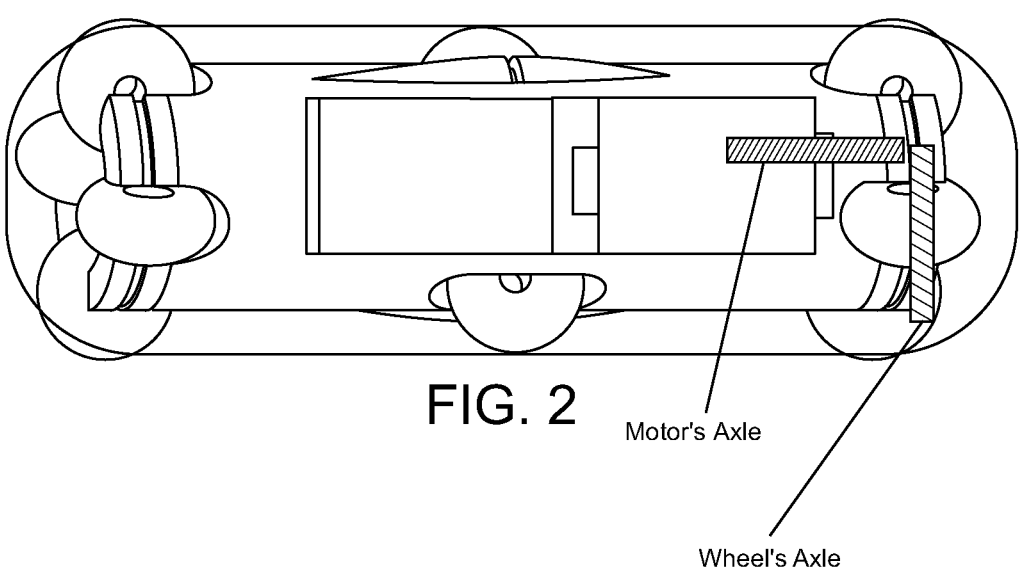

FIG. 2 shows the geometric relationship between motor's axle and wheel's axle of a toroidal vehicle.

Figures 3, 4:
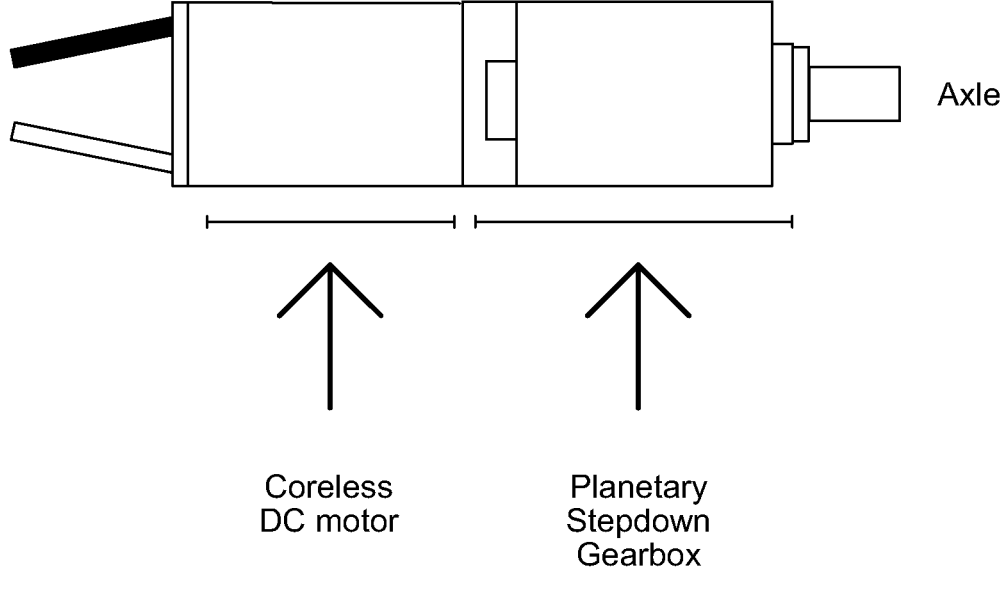

FIG. 3 shows a basic DC motor, planetary gears, and axle.

FIG. 4 shows an example of a toroidal vehicle with two motors.

Figure 5:
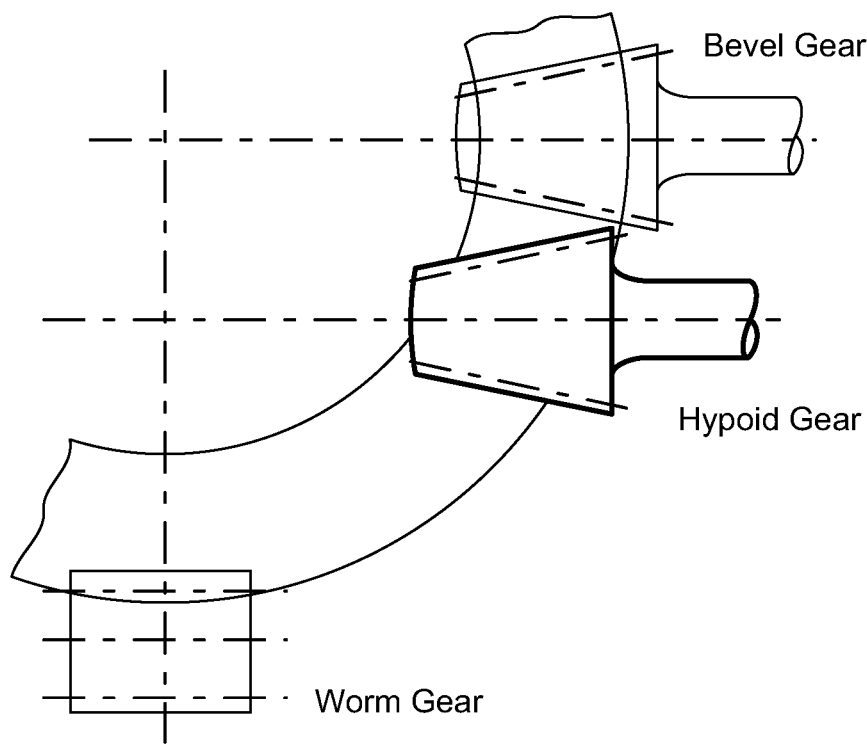

FIG. 5 depicts the site of contact of motor axle with wheel for a worm gear, hypoid gear and bevel gear.

Figure 6A:
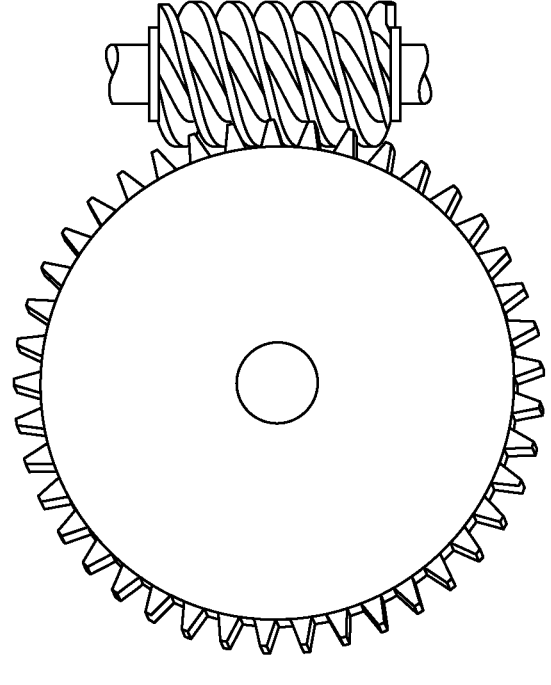

FIG. 6a depicts an example of a worm gear that may be used in conjunction with the present invention.

Figure 6B:
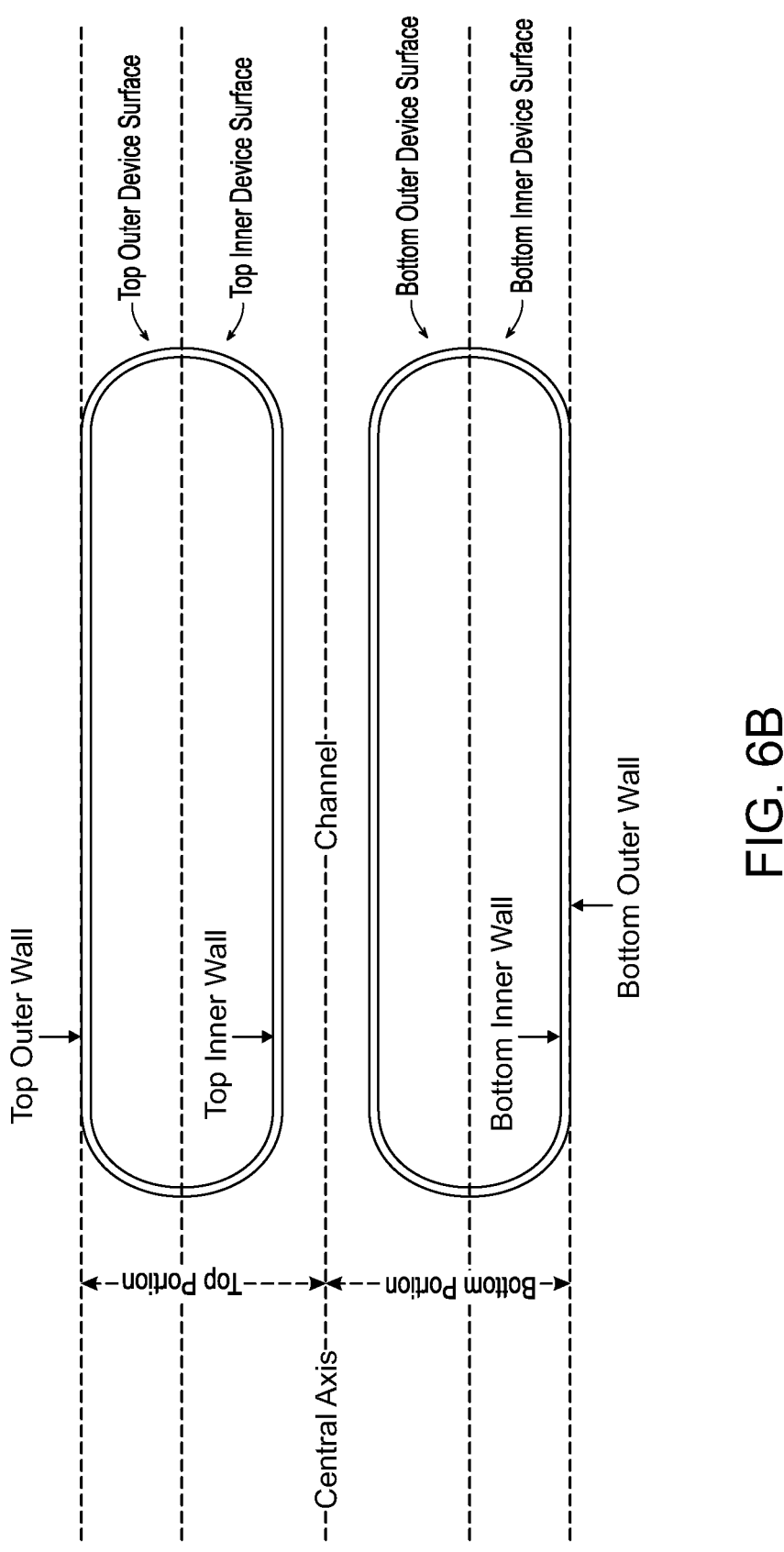

FIG. 6b depicts a cross-section of the present invention's toroidal vehicle with the following terminology used to describe the various embodiments of the present invention.

Figure 6C:
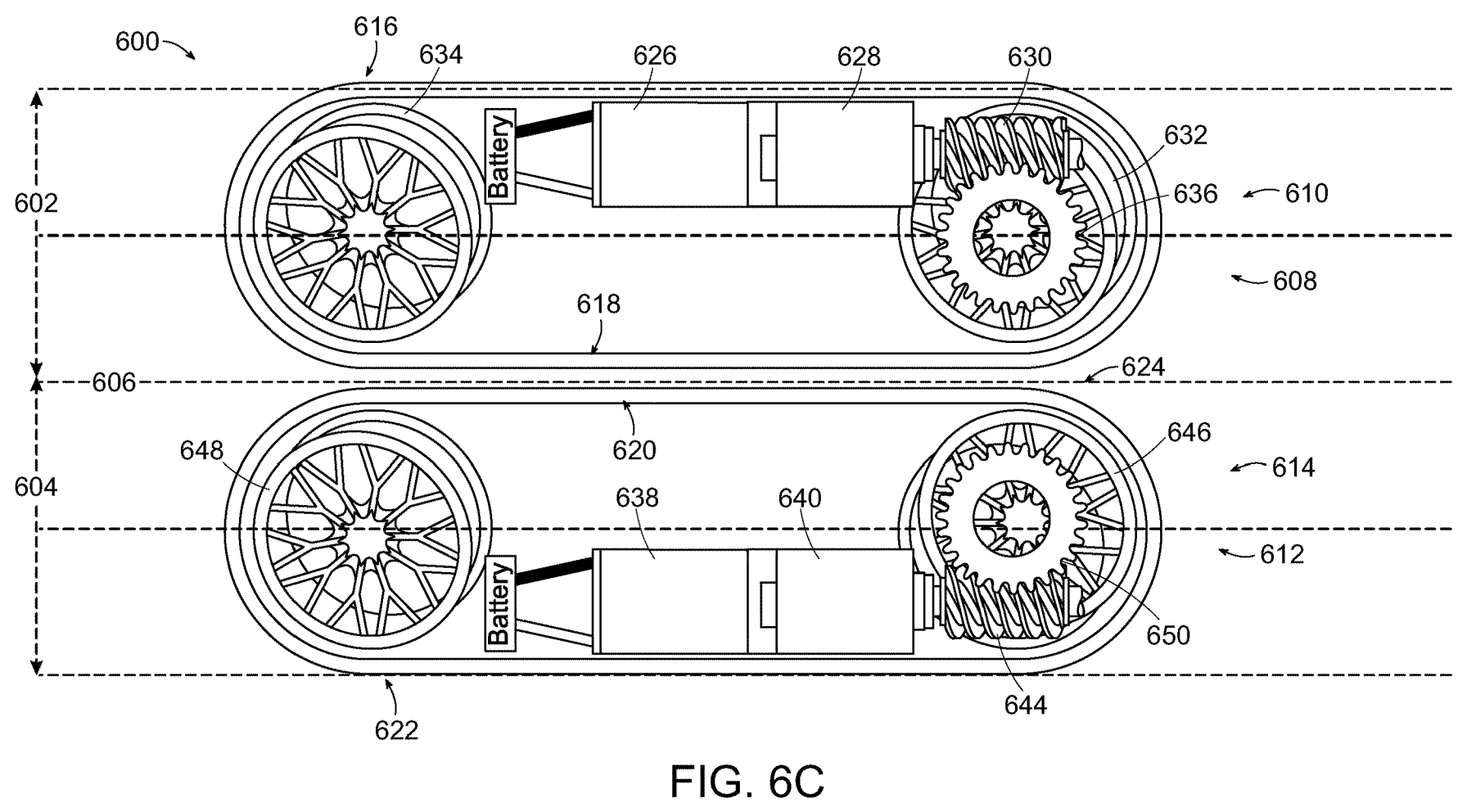

FIG. 6c depicts an embodiment of a toroidal vehicle having a worm gear in a top portion of the toroidal vehicle and having another worm gear in a bottom portion of the toroidal vehicle.

Figures 7A, 7B:
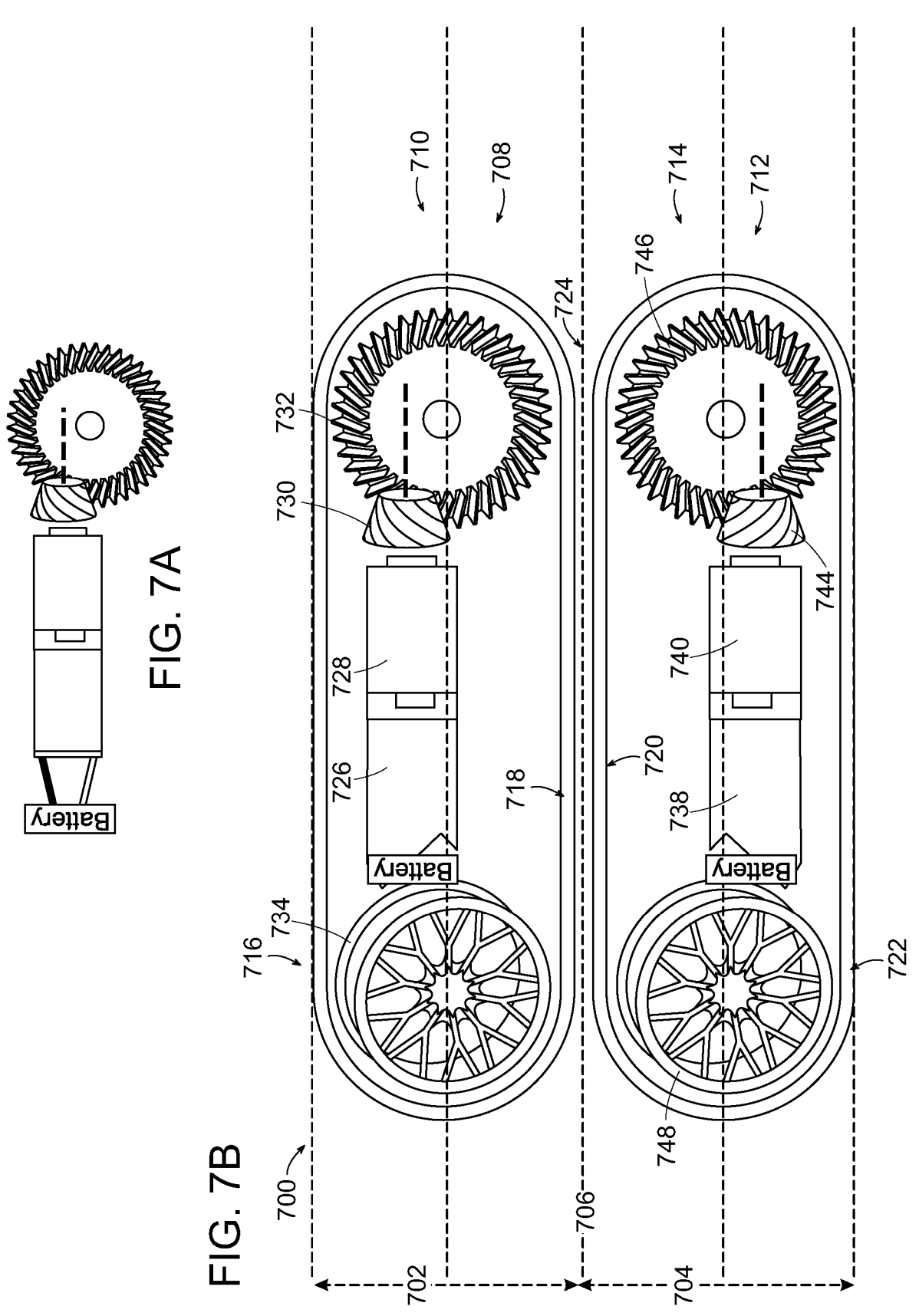

FIG. 7a depicts another configuration using a hypoid gear.

FIG. 7b depicts an embodiment of a toroidal vehicle having a hypoid gear in a top portion of the toroidal vehicle and having another hypoid gear in a bottom portion of the toroidal vehicle.

Figures 8A, 8B:
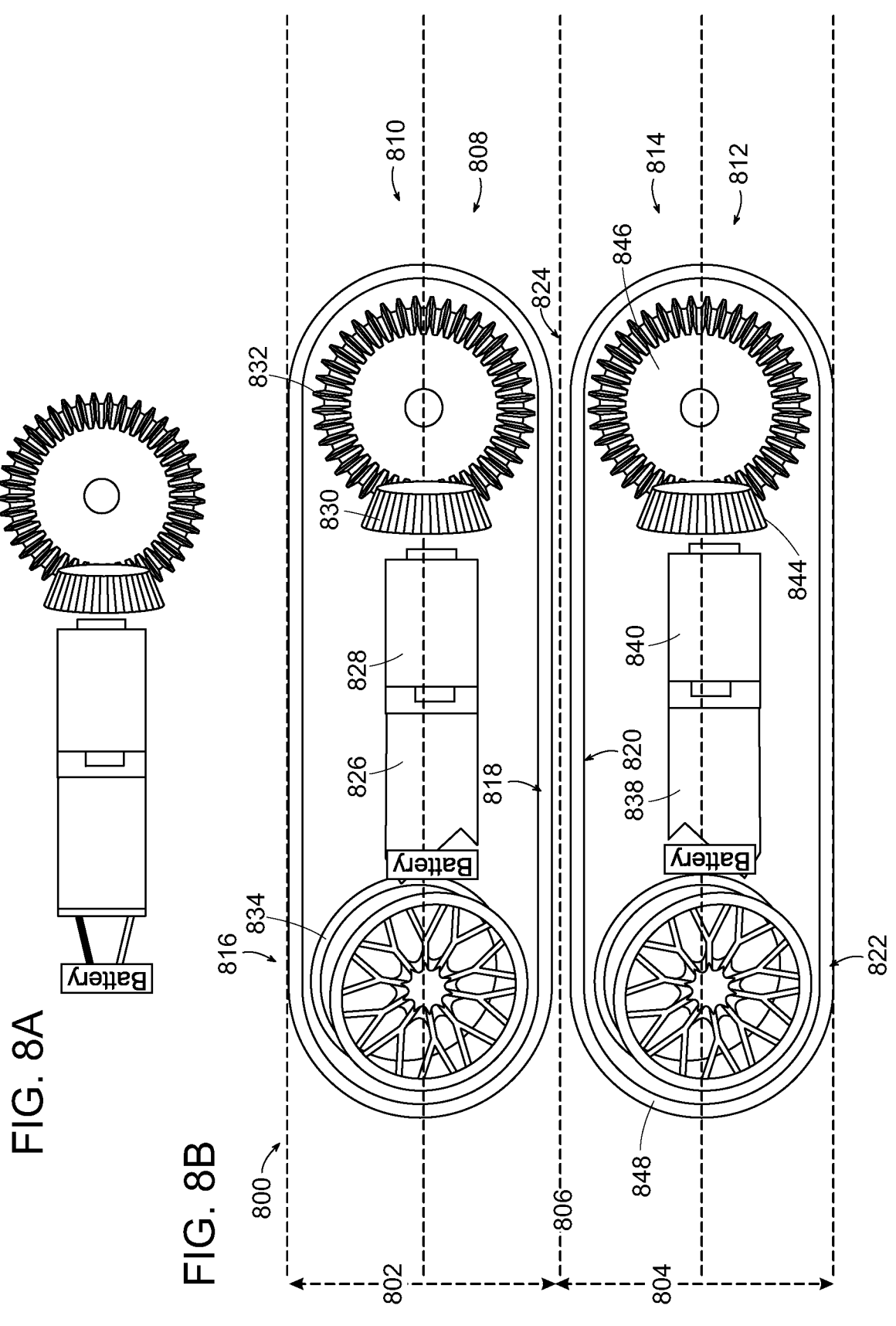

FIG. 8a depicts another configuration that utilizes a bevel gear in a toroidal vehicle.

FIG. 8b depicts an embodiment of a toroidal vehicle having a bevel gear in a top portion of the toroidal vehicle and having another bevel gear in a bottom portion of the toroidal vehicle.

Figures 9A, 9B:
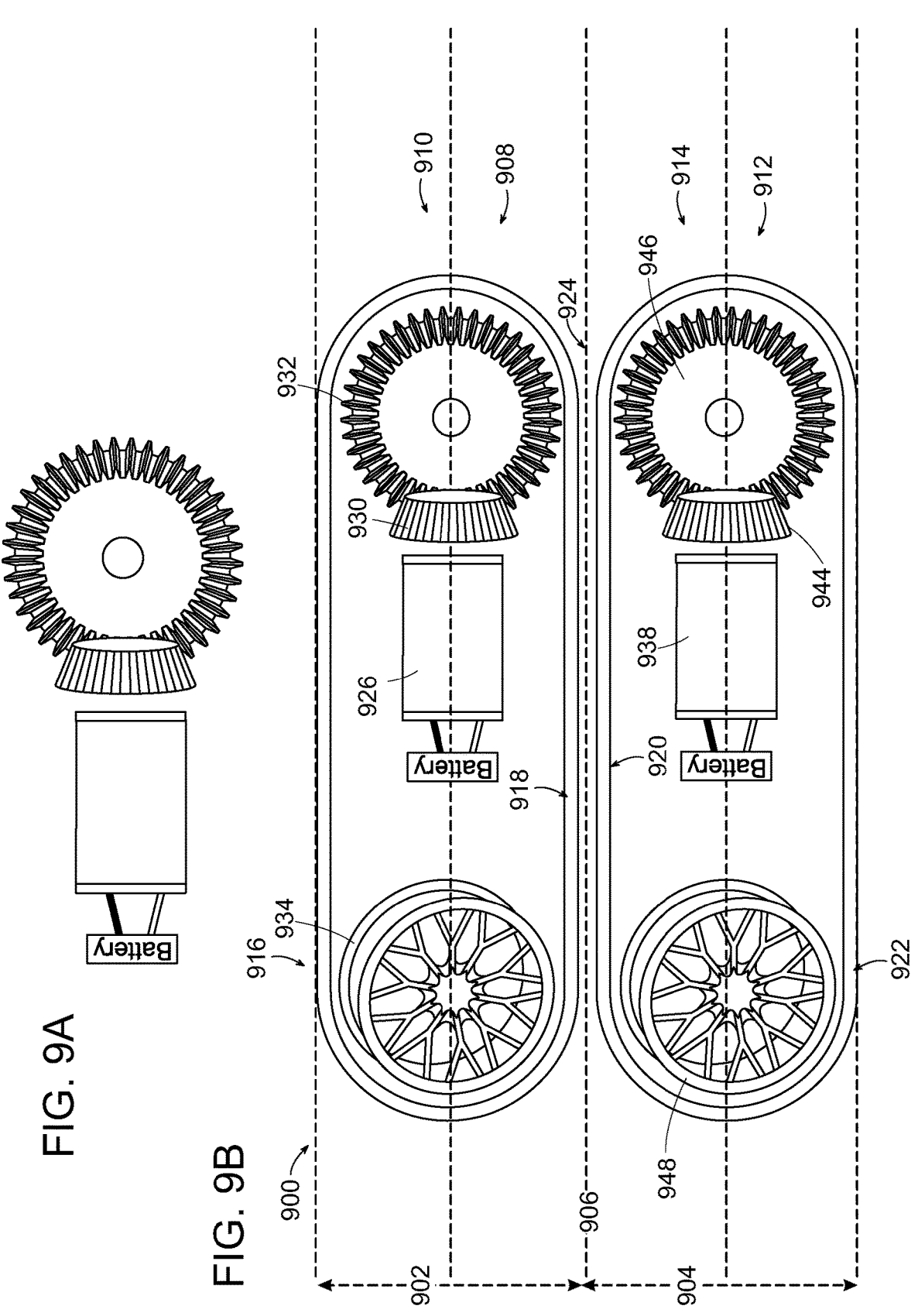

FIG. 9a depicts a bevel gear configuration that shows the motor without the planetary step-down gears.

FIG. 9b depicts an embodiment of a toroidal vehicle having a bevel gear in a top portion of the toroidal vehicle and having another bevel gear in a bottom portion of the toroidal vehicle.

Figures 10, 11A, 11B, 11C, 11D, 11E, 11F:
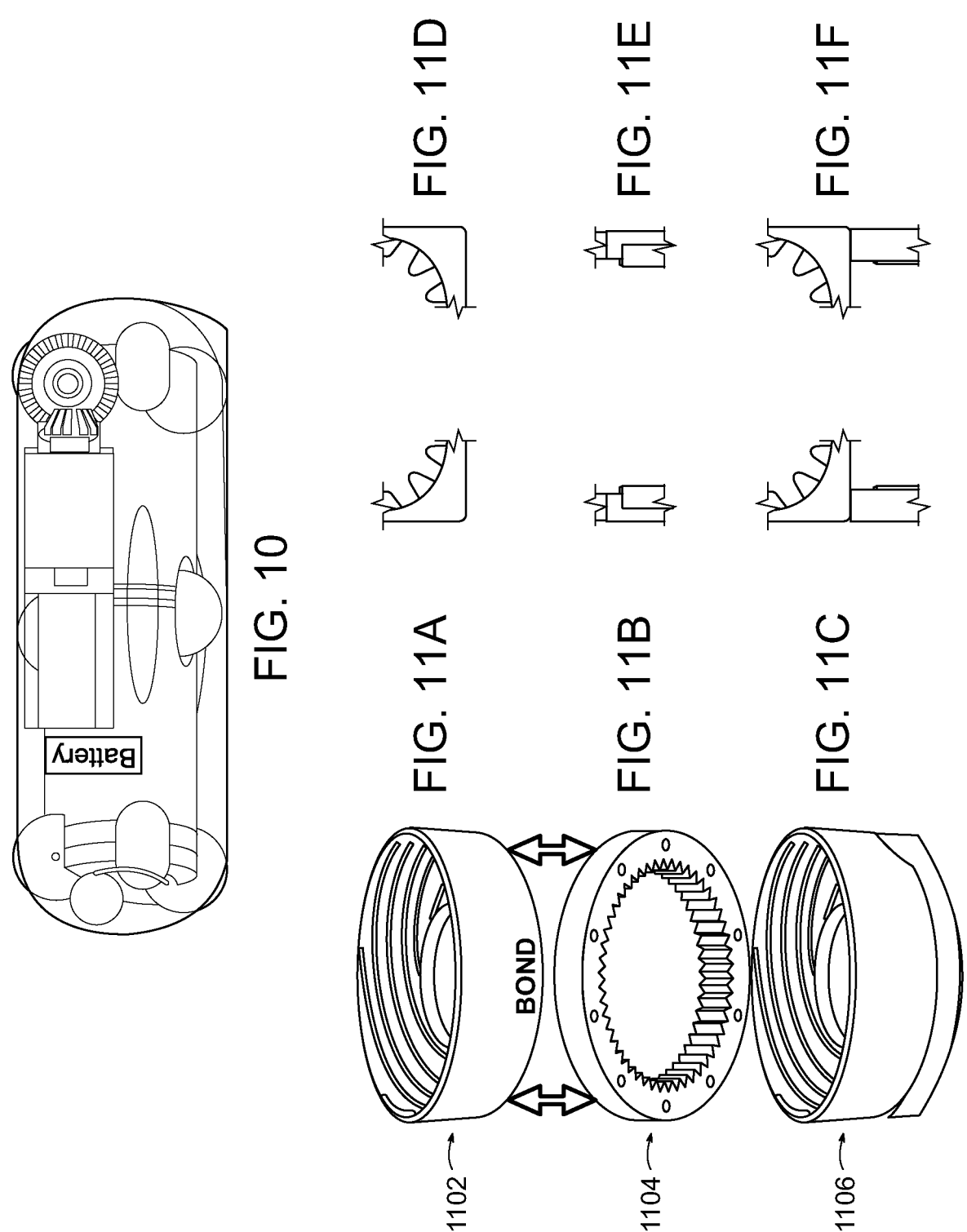

FIG. 10 depicts a toroidal vehicle containing one drive train.

FIG. 11a shows an internal curved spiral gear.

FIG. 11b shows an internal spur gear.

FIG. 11c shows the combined ICS/IS gear unit.

FIG. 11d shows a cross-sectional view of FIG. 11a.

FIG. 11e shows a cross-sectional view of FIG. 11b.

FIG. 11f shows a cross-sectional view of FIG. 11c.

Figures 12A, 12B, 13A, 13B:
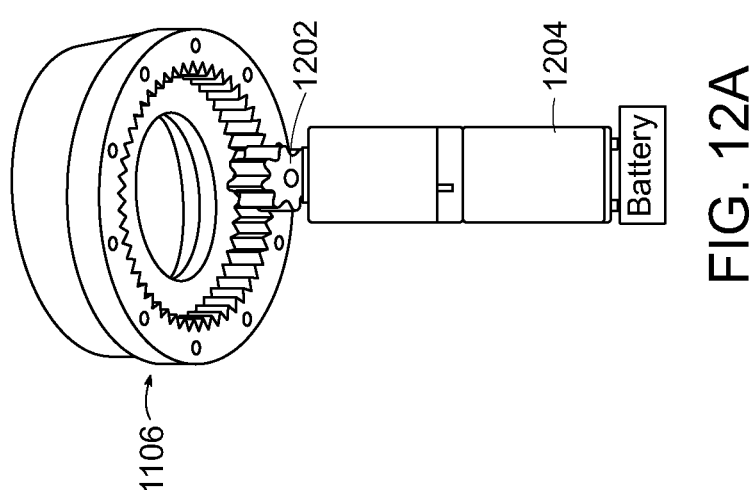

FIG. 12a depicts a simple spur gear located on the motor's output axle, where the spur gear engages the IS gear of the combined ICS/IS gear unit shown in FIG. 11c.

FIG. 12b shows the rotation of ICS/IS gear results in the rotation of wheels.

FIG. 13a depicts the curved spiral aspect of the ICS/IS gear combination gear that meshes with a plurality of wheels.

FIG. 13b depicts two motors that engage the IS gear.

Figure 14A:
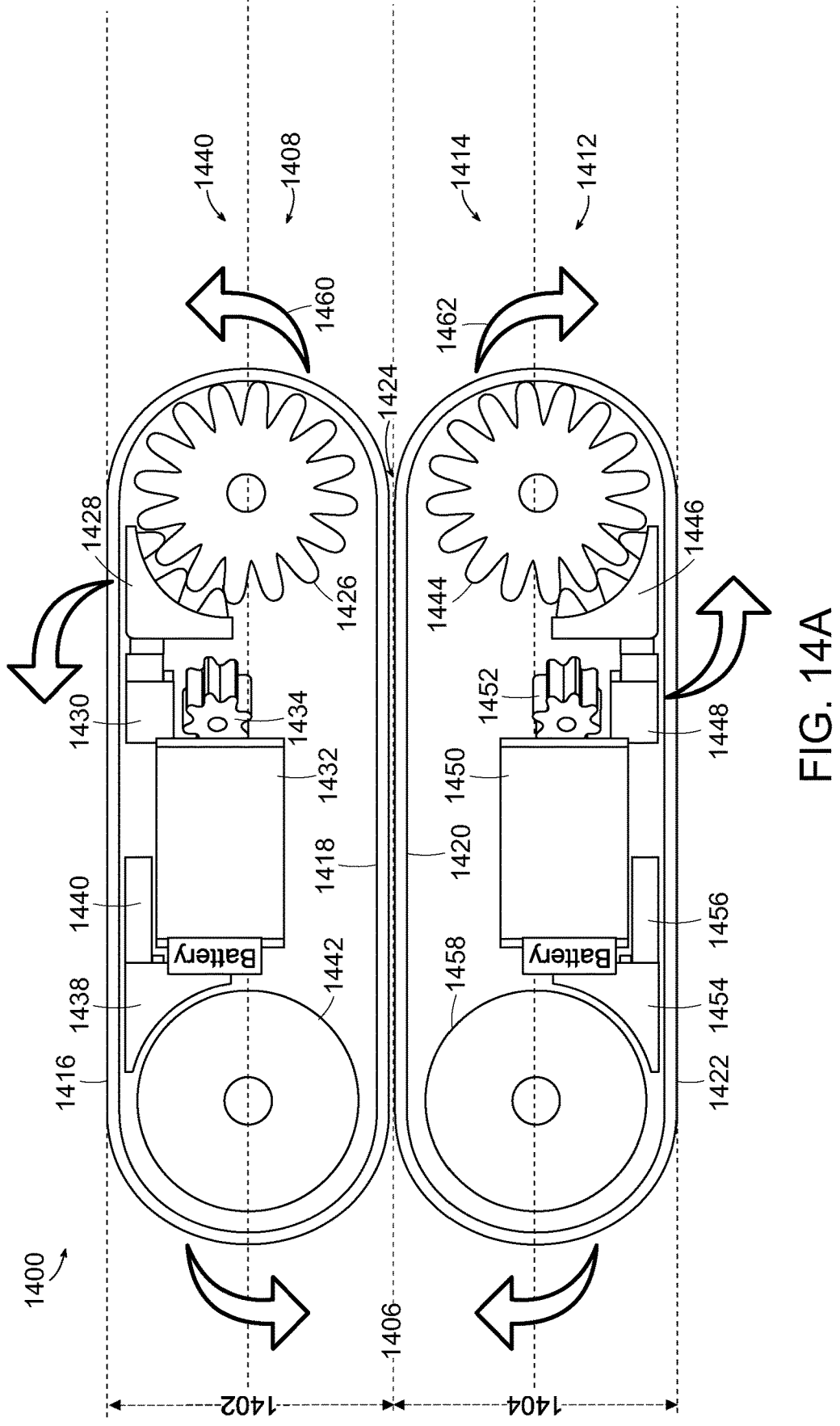

FIG. 14a depicts a cross-section of one embodiment of the present invention's vehicle where a relatively slower motor speed may allow a DC motor to be directly coupled to a ICS/IS gear (without planetary gear) in the toroidal vehicle.

Figure 14B:
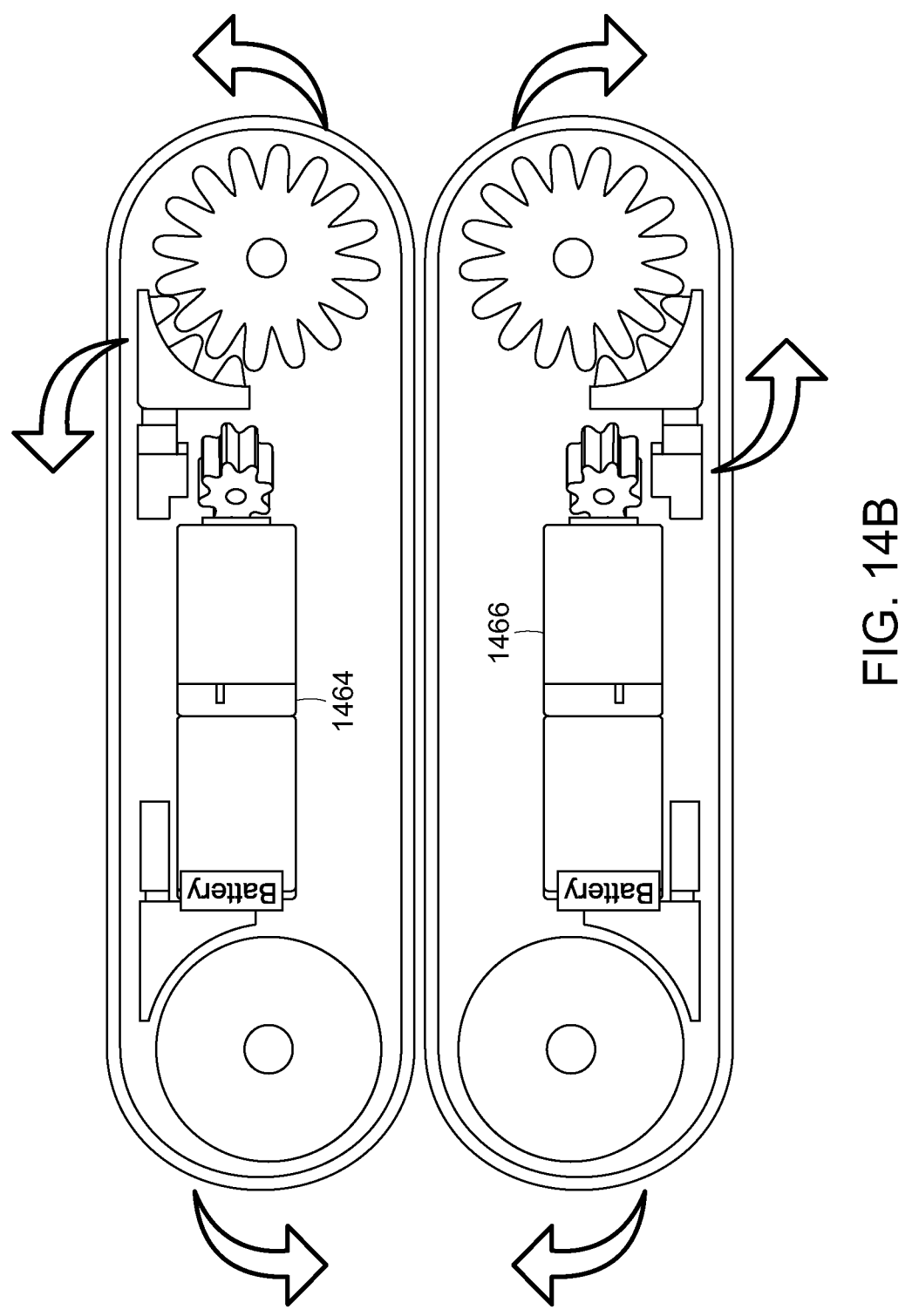

FIG. 14b depicts an extension to the embodiment depicted in FIG. 14a, with the inclusion of planetary gears.

Figure 15:
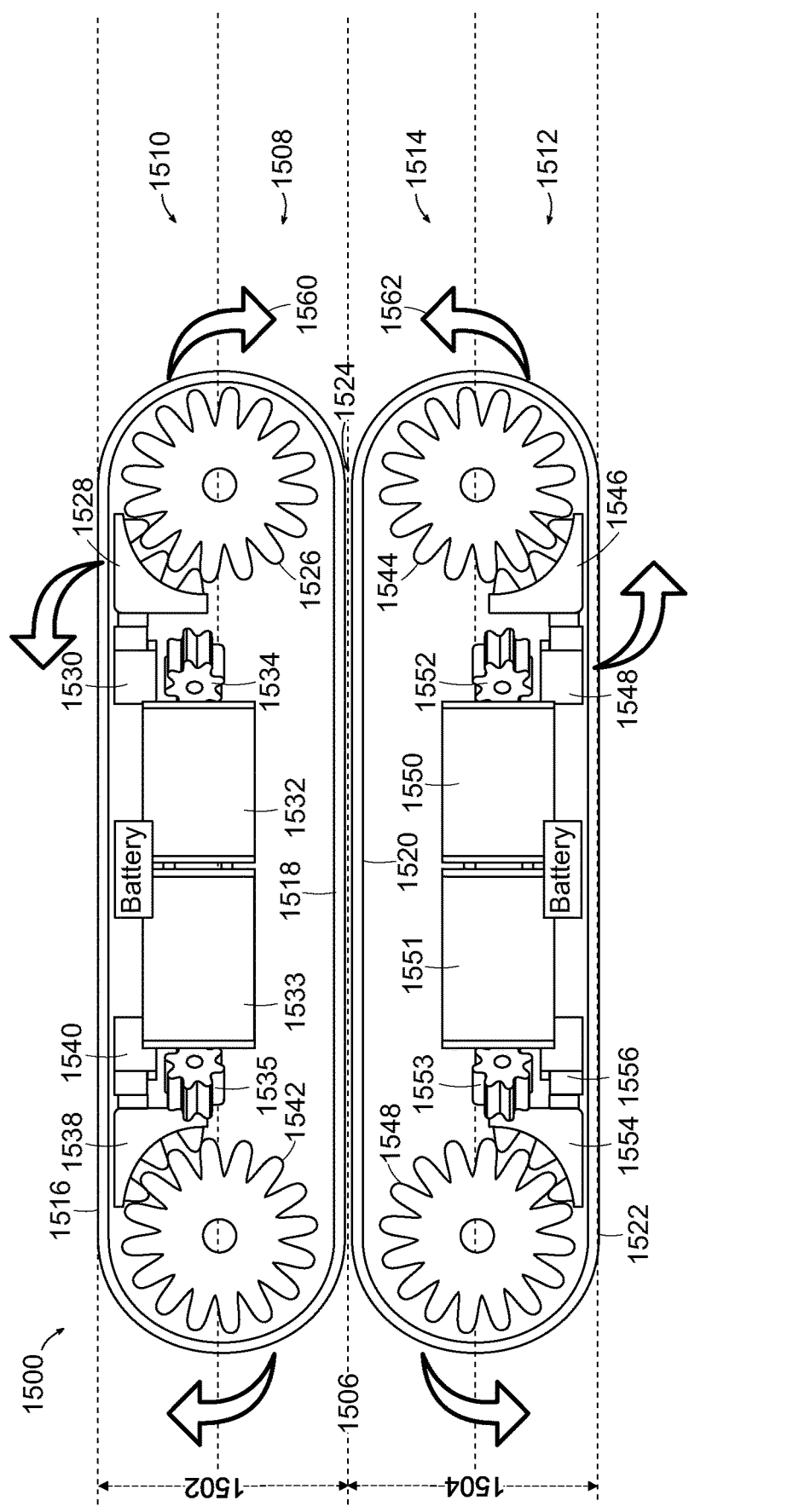

FIG. 15 depicts two motors without planetary gears and two ICS/IS gears in a toroidal vehicle.

Figures 16A, 16B, 16C:
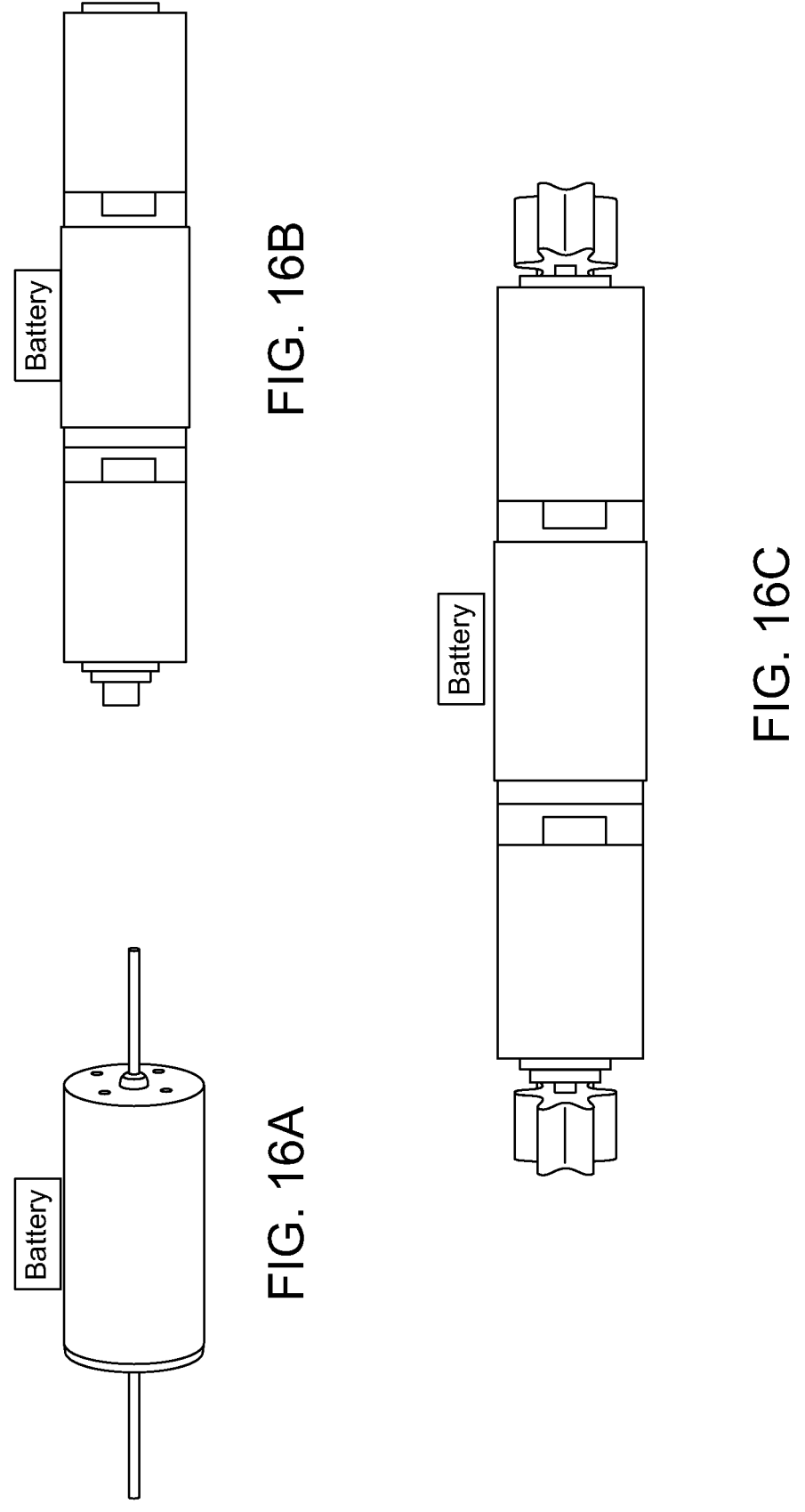

FIG. 16a depicts a double-axle motor.

6

FIG. 16b depicts the double-axle motor of FIG. 16a equipped with a planetary gearbox at each axle.

FIG. 16c depicts the double-axle motor of FIG. 16b with the pair of planetary gearboxes along with a pair of spur gears.

Figures 17A, 17B:
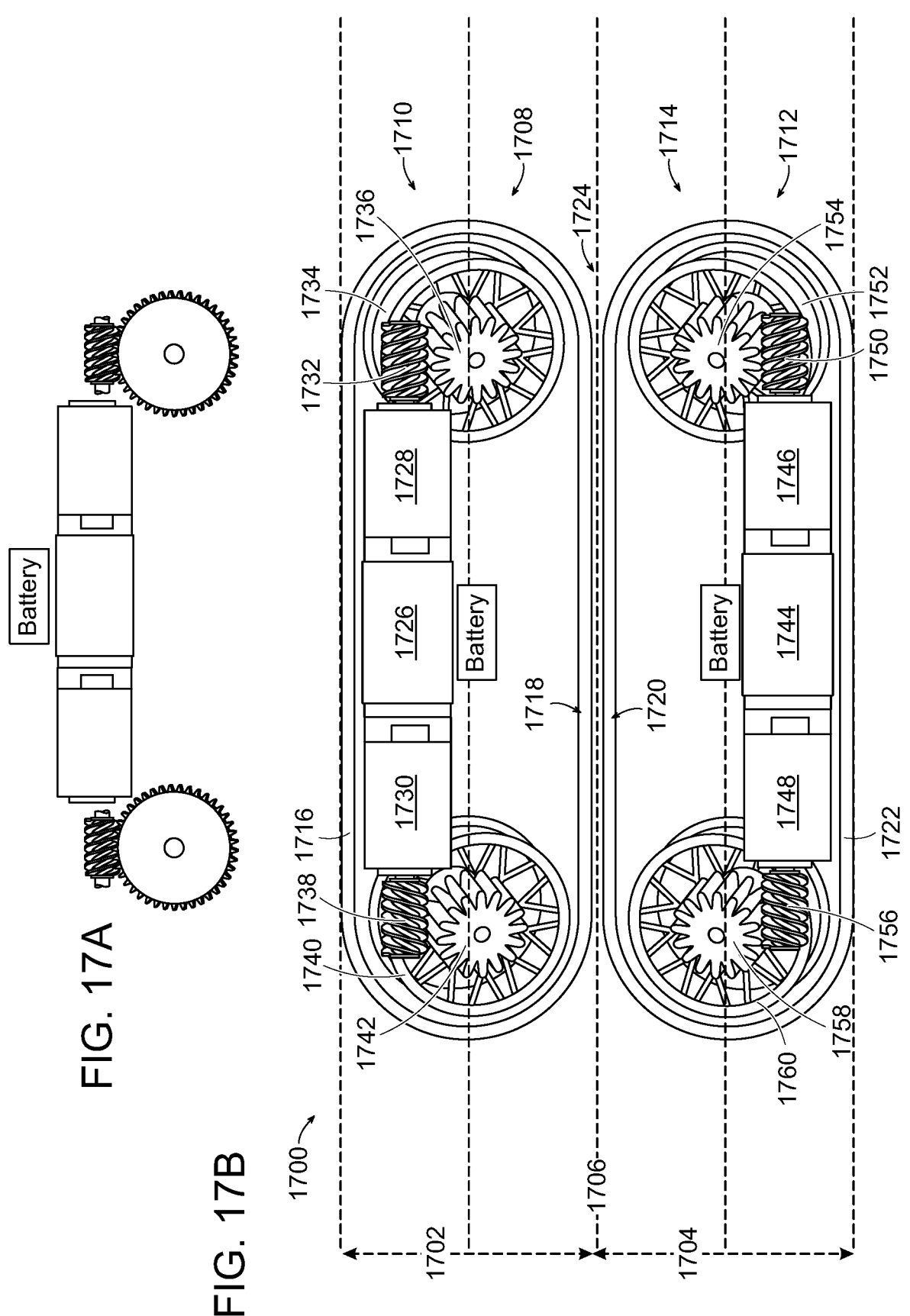

FIG. 17a depicts a double-axle motor with a pair of planetary gearboxes on either side, along with a worm gear mounted on either side of the motor.

FIG. 17b depicts an embodiment of a toroidal vehicle having two such worm gears in a top portion of the toroidal vehicle and having two such worm gears in a bottom portion of the toroidal vehicle.

Figures 18A, 18B:
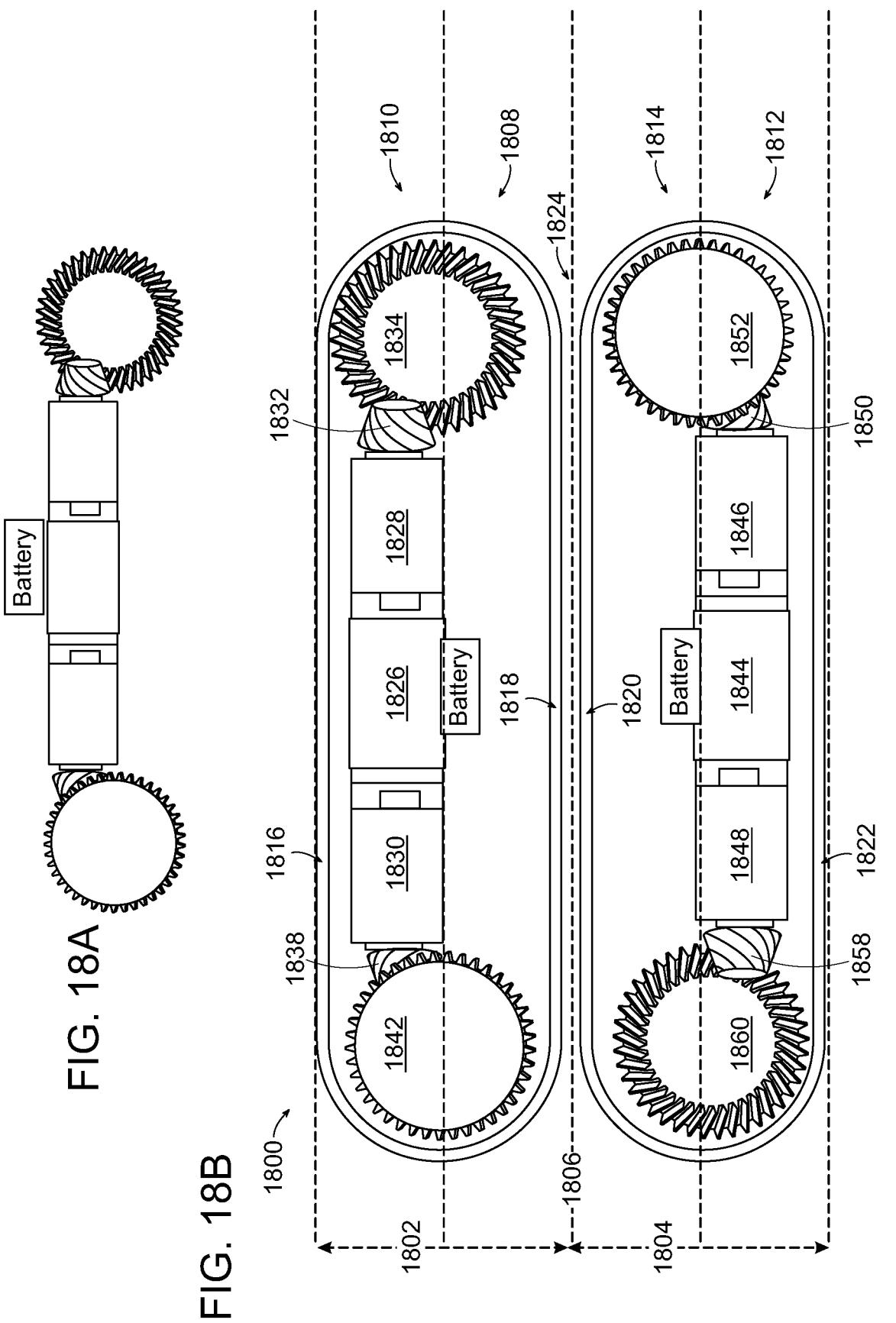

FIG. 18a depicts a double-axle motor with a pair of planetary gearboxes on either side, along with a hypoid gear mounted on either side of the motor.

FIG. 18b depicts an embodiment of a toroidal vehicle having two such hypoid gears in a top portion of the toroidal vehicle and having two such hypoid gears in a bottom portion of the toroidal vehicle.

Figures 19A, 19B:
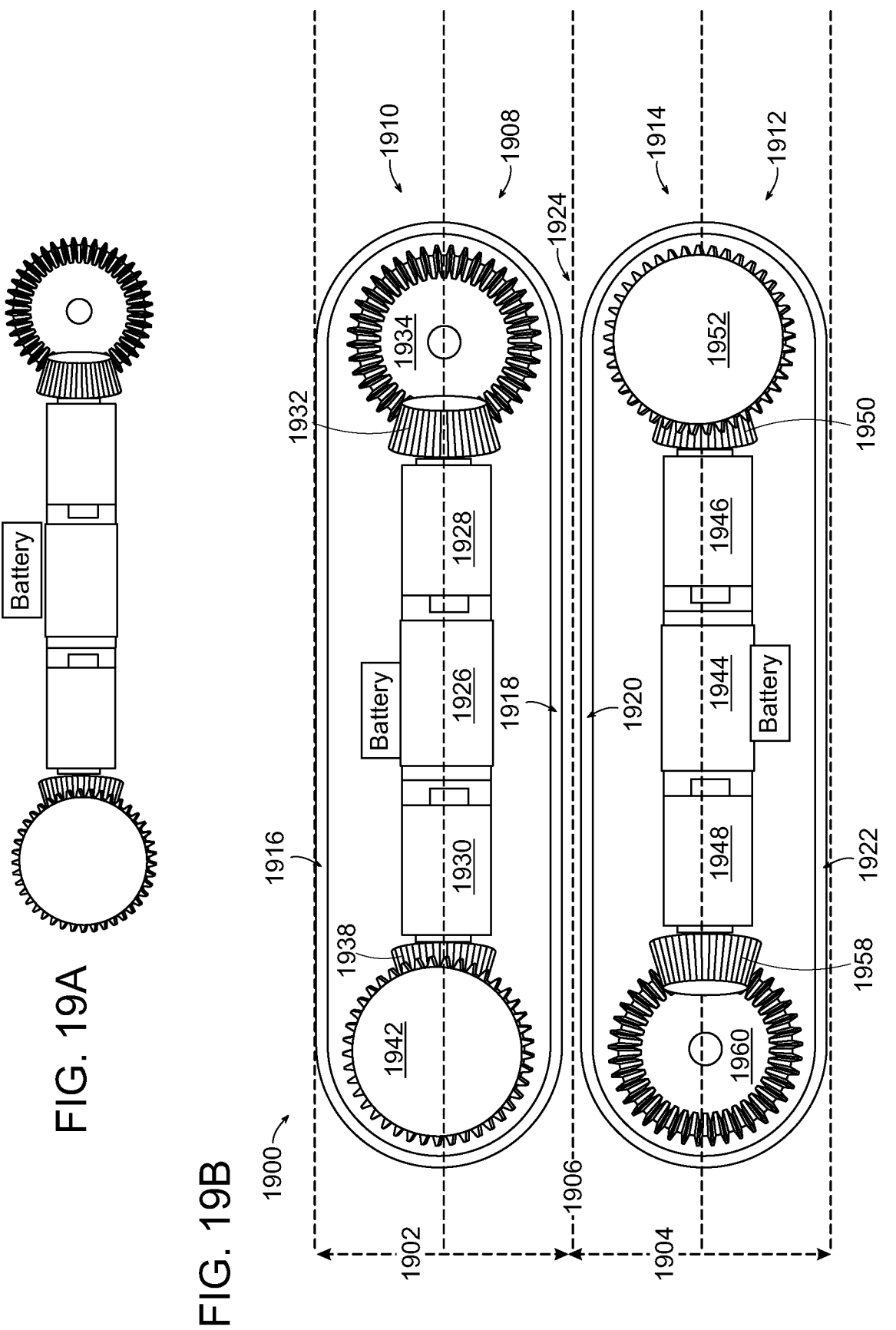

FIG. 19a depicts a double-axle motor with a pair of planetary gearboxes on either side, along with a bevel gear mounted on either side of the motor.

FIG. 19b depicts an embodiment of a toroidal vehicle having two such bevel gears in a top portion of the toroidal vehicle and having two such bevel gears in a bottom portion of the toroidal vehicle.

Figures 20A, 20B, 20C:
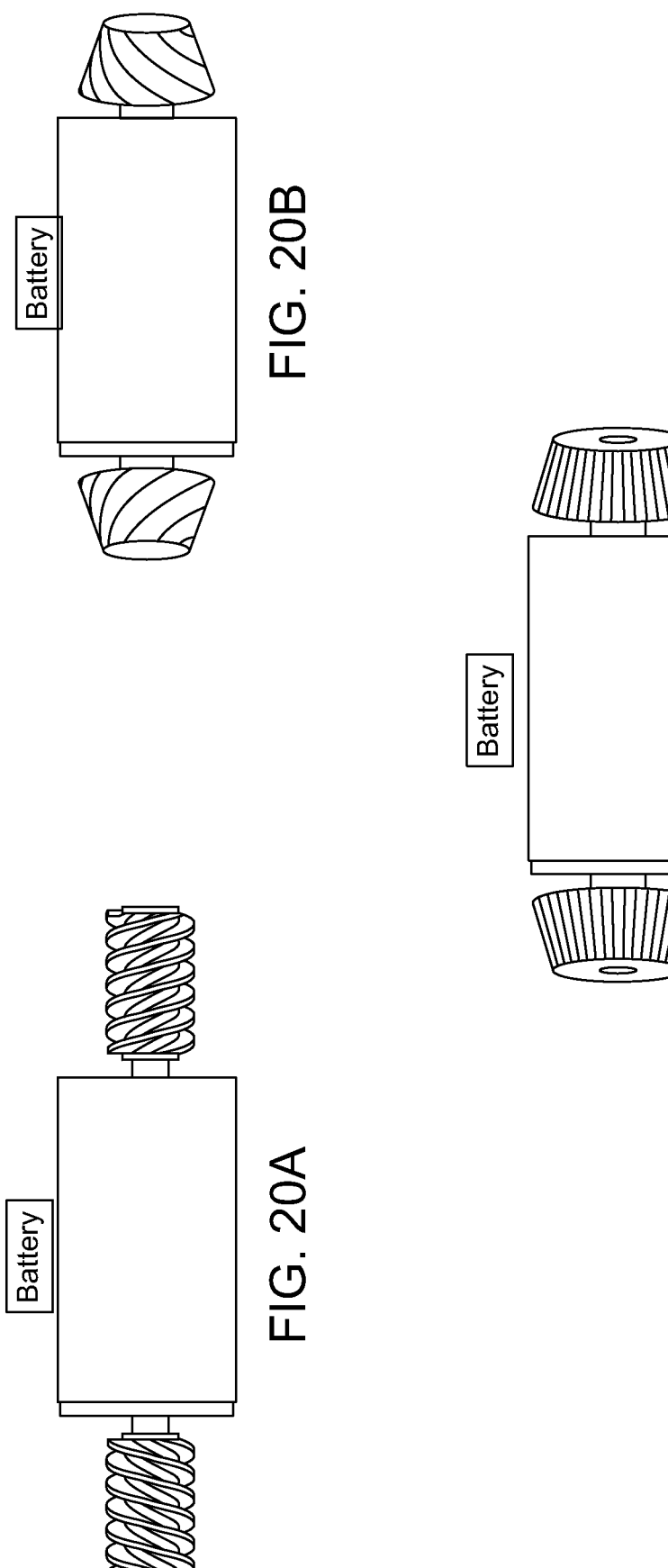

FIG. 20a depicts a double-axle motor with a worm gear on either side.

FIG. 20b depicts a double-axle motor with a hypoid gear on either side.

FIG. 20c depicts a double-axle motor with a bevel gear on either side.

Figures 21A, 21B:
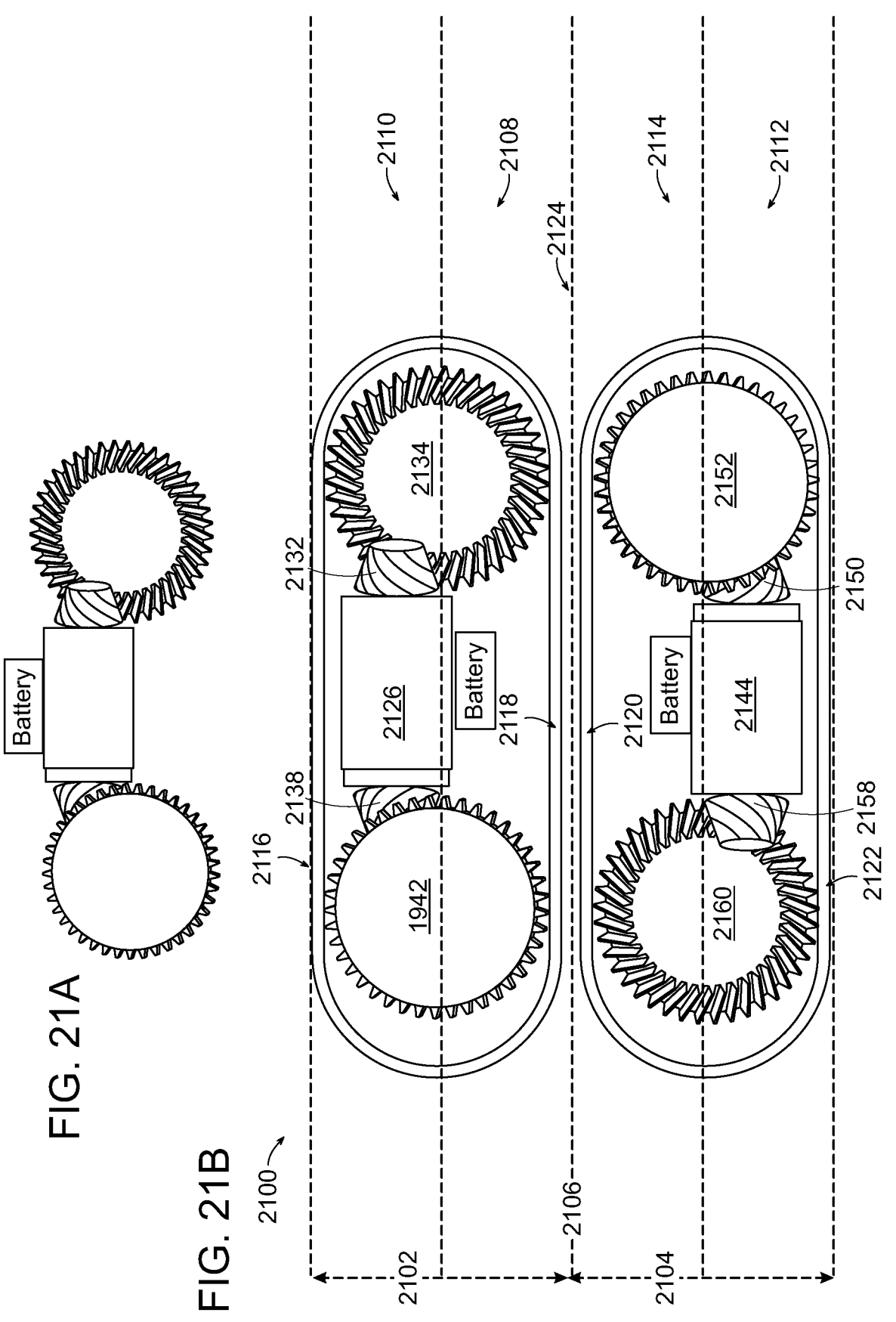

FIG. 21a depicts a double-axle motor with a pair of hypoid gears mounted on either side of the motor.

FIG. 21b depicts an embodiment of a toroidal vehicle without planetary gears having two such hypoid gears in a top portion of the toroidal vehicle and having two such hypoid gears in a bottom portion of the toroidal vehicle.

Figure 22:
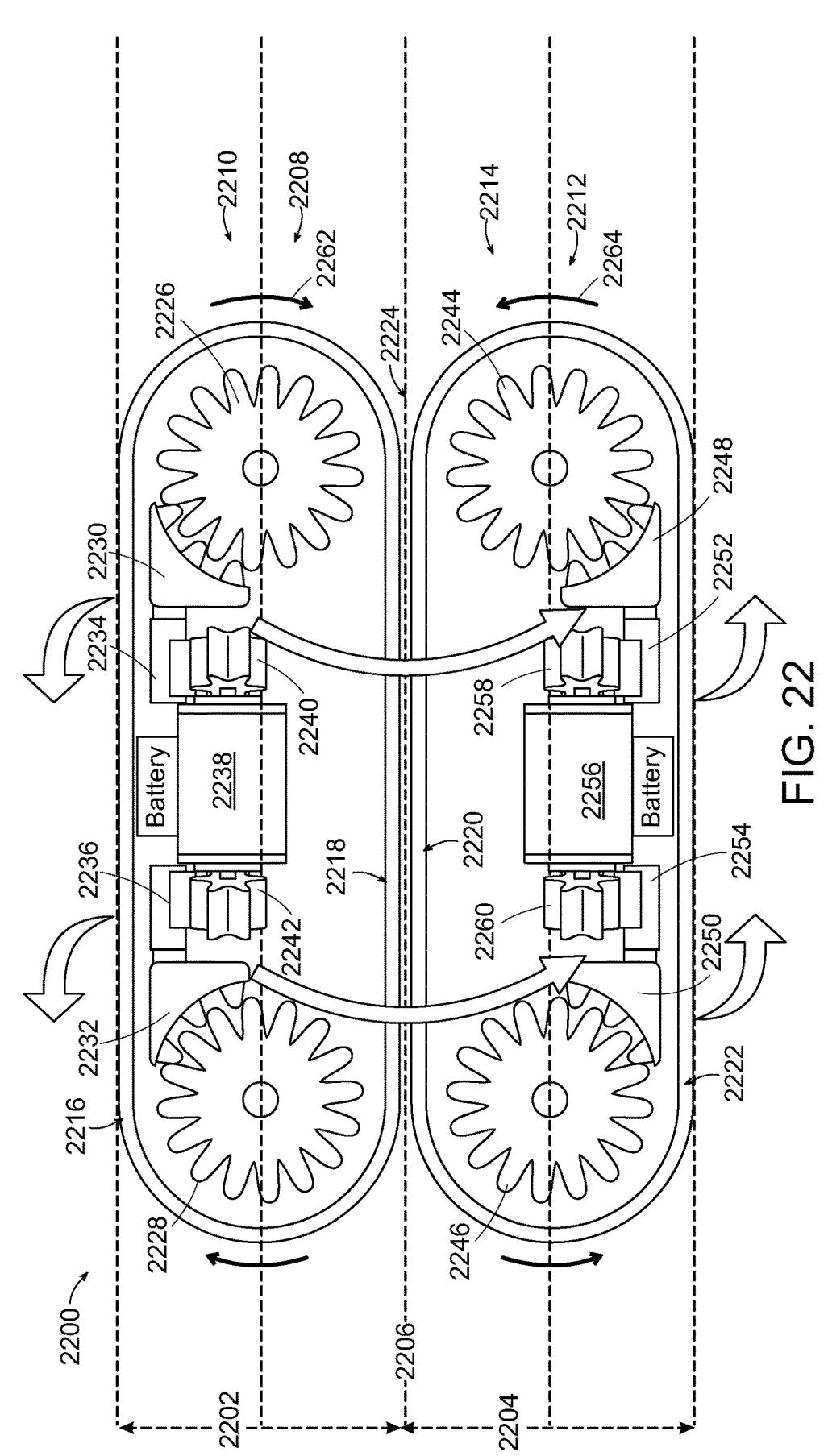

FIG. 22 depicts a double-axle motor without planetary gearboxes and an ICS/IS gear driving both front and rear wheels.

DETAILED DESCRIPTION

While this invention is illustrated and described in a preferred embodiment, the invention may be produced in many different configurations. There is depicted in the drawings, and will herein be described in detail, a preferred embodiment of the invention, with the understanding that the present disclosure is to be considered as an exemplification of the principles of the invention and the associated functional specifications for its construction and is not intended to limit the invention to the embodiment illustrated. Those skilled in the art will envision many other possible variations within the scope of the present invention.

Note that in this description, references to "one embodiment" or "an embodiment" mean that the feature being referred to is included in at least one embodiment of the invention. Further, separate references to "one embodiment" in this description do not necessarily refer to the same embodiment; however, neither are such embodiments mutually exclusive, unless so stated and except as will be readily apparent to those of ordinary skill in the art. Thus, the present invention can include any variety of combinations and/or integrations of the embodiments described herein.

In prior art systems, there is no disclosure for gear systems for use in toroidal systems. Properties of the toroidal vehicle require a unique configuration of motor(s) and drivetrain(s) that are attached to the vehicle's roughly cylindrical frame and rotate radially arranged wheels located at each end of the vehicle. In addition, the existing motors that are sufficiently small for a vehicle to traverse a small space (such as one to traverse intestines) spin at a rate where a significant step-down in gears is necessary. The novel motor and drivetrain systems described here are configured to function in the protected space within a toroidal tread and on a small scale.

FIG. 1 is one version of a vehicle driven by a toroidal tread (similar to one described in Massicotte's U.S. Pat. No. 9,693,676). The vehicle depicted in FIG. 1 comprises a plurality of wheels, one of which is labeled 1a, an outside wall 1b of the toroidal tread, a direct current (DC) motor 1c with step-down planetary gear, and a frame of the toroidal vehicle 1d to which the motor, the drive train, the wheels, the power supply, and electronics associated with the vehicle are attached.

FIG. 2 depicts the orientation of the motor with respect to the driven wheels. FIG. 2 is an example of a toroid drone showing only limited internal components. It should be noted that the motor's axle is perpendicular to the wheel's axle.

As noted in U.S. Pat. No. 9,693,676, the vehicle moves with the rotation of a toroidal tread which can be considered a military tank tread rotated axially in 360 degrees. As with a military tank, the tread is rotated by an internal mechanism. Since the toroidal tread is three-dimensional, a novel arrangement of internal components is necessary. The space within a toroidal balloon is a cylinder whose wall thickness is determined by the wheels' diameter. The frame, motor, power supply, drivetrain, and electronic components must be configured to fit within this internal cylindrical space.

The motor types small enough to fit within the internal space within the toroidal tread are coreless motors that rotate at extremely high velocities (typically 10,000-50,000 rpm). These motors are available commercially with attached planetary motors with reduction ratios of 1:3-1:1000, but typically 1:200 for this indication and are shown in FIG. 3. The combination of coreless motor and planetary motor and available off the shelf and no claim is made in this Patent Application.

Still, with the coreless motor attached to a planetary gearbox, the rotational output is too fast for the toroidal vehicle's rotational wheels, so another system of step-down gears is necessary in combination with the motor or motor/planetary complex. One novelty in the drive train claimed in this application is related to the great step-down in gear systems for a high-spinning coreless motor to slow-spinning wheels in a toroidal vehicle. In the novel toroidal vehicle, the motor sits longitudinally on the vehicle's frame. The plurality of wheels rotate at each of the two ends of the frame and radially with axles perpendicular to the motor's axle. In one example in FIG. 4, two motors drive two of four wheels at one end and no wheels at the other end of a cylindrical frame. FIG. 4 is included as an example to show the relationship between the motor/planetary complex with the wheels of the vehicle.

One technical challenge addressed with this patent application is the mechanical connection between the spinning output of the motor and the vehicle's wheels, with a few options being proposed herein for the complete drivetrain.

In one configuration, the motor's axle spins a wheel directly where the wheel is itself a gear. Different gear configurations may accomplish this transition and also provide step-down in rotational output. FIG. 5 shows the site of the meshing of the motor axle gear with the vehicle's wheel for a worm gear, a hypoid gear, and a bevel gear.

FIG. 6a depicts an example of a worm gear that may be used in conjunction with the present invention. FIG. 6c shows two worm gear systems in a toroidal vehicle. Note that a spur gear is attached co-axially to the spinning wheel. The spur gear is of small diameter than the wheel's diameter so the screw aspect of the motor gear does not interfere with the tread rotating over the wheel.

FIG. 6b depicts a cross-section of the present invention's toroidal vehicle with the following terminology used to describe the various embodiments of the present invention: central axis, a top portion, and a bottom portion that is symmetric about the central axis shown. The top portion having a top outer device surface and a top inner device surface, where both the top inner device surface and the top outer device surface comprise a top inner wall and a top outer wall. Similarly, the bottom portion has a bottom outer device surface and a bottom inner device surface, where both the bottom inner device surface and the bottom outer device surface comprise a bottom inner wall and a bottom outer wall. As depicted in FIG. 13c, a portion of the top inner device surface and the bottom inner device surface adjacent to each other form a channel.

FIG. 6c depicts an embodiment of a toroidal vehicle having a worm gear in a top portion of the toroidal vehicle and having another worm gear in a bottom portion of the toroidal vehicle. In the embodiment depicted in FIG. 6c, the present invention provides a toroidal device 600 having a top portion 602 and a bottom portion 604 that are symmetric about a central axis 606, where the top portion 602 has a top inner device surface 608 and a top outer device surface 610 and the bottom portion 604 has a bottom inner device surface 614 and a bottom outer device surface 612, each of the top inner device surface 608 and top outer device surface 610 having a top inner wall 618 and a top outer wall 616 and each of the bottom inner device surface 614 and bottom outer device surface 612 comprising a bottom inner wall 620 and a bottom outer wall 622, where a portion of the top outer wall 616 associated with the top inner device surface 608 and another portion of the bottom outer wall 622 associated with the bottom inner device surface 614 are adjacent to each other and are configured to form a channel 624.

Enclosed within the top inner wall 618 is a single-axle DC motor 626 having a planetary gearbox 628, on which is mounted a worm gear 630. Also enclosed within the top inner walls 618 are a pair of wheels 632 and 634, with wheel 632 having a gear wheel 636 mounted thereon. When energized by motor 626, worm gear 630 engages the gears on the gear wheel 636, causing a rotational movement, which then rotates the wheel 632, which also results in the rotation of wheel 634.

Enclosed within the bottom inner wall 620 is a single-axle DC motor 638 having a planetary gearbox 640, on which is mounted a worm gear 644. Also enclosed within the top inner walls 620 are a pair of wheels 646 and 648, with wheel 646 having a gear wheel 650 mounted thereon. When energized by motor 638, worm gear 644 engages the gears on the gear wheel 650, causing a rotational movement, which then rotates the wheel 646, which also results in the rotation of wheel 648.

The single-axle DC motor 626 causes the wheels 632, 634 to move rotationally in a first direction, resulting in a first inversion of the top inner device surface 608 and the top outer device surface 610, and the single-axle DC motor 638 causes the wheels 646, 648 to move rotationally in a second direction, resulting in a second inversion of the bottom inner device surface 614 and the bottom outer device surface 612, where the first direction is opposite that of the second direction. The first and second inversions safely propel the device 600 without sliding of the top and bottom outer device surfaces 610, 612 against any contacted external wall and allowing low friction movement of the device.

Additional components not shown in the figures may be part of the toroidal vehicle. Non-limiting examples of such components include, but are not limited to, one or more power sources (depicted as one or more batteries), one or more lenses, one or more illuminating LEDs, a CMOS imager, an Application-Specific Integrated Circuits (ASIC) transmitter, an antenna and a cylindrical frame to support those internal components. Any of these components or combinations of these components could be incorporated as part of the toroidal vehicle. Additionally, the motors described below are powered through onboard power sources, such as one or batteries. The number of batteries used should not be used to limit the scope of the invention, FIG. 7a depicts another configuration using a hypoid gear. This configuration allows the motor's axle to spin above the level of the wheel's axle and provides a step-down in rotational output.

FIG. 7b depicts an embodiment of a toroidal vehicle having a hypoid gear in a top portion of the toroidal vehicle and having another hypoid gear in a bottom portion of the toroidal vehicle. In the embodiment depicted in FIG. 7b, the present invention provides a toroidal device 700 having a top portion 702 and a bottom portion 704 that are symmetric about a central axis 706, where the top portion 702 has a top inner device surface 708 and a top outer device surface 710 and the bottom portion 704 has a bottom inner device surface 714 and a bottom outer device surface 712, each of the top inner device surface 708 and top outer device surface 710 having a top inner wall 718 and a top outer wall 716 and each of the bottom inner device surface 714 and bottom outer device surface 712 comprising a bottom inner wall 720 and a bottom outer wall 722, where a portion of the top outer wall 716 associated with the top inner device surface 708 and another portion of the bottom outer wall 722 associated with the bottom inner device surface 714 are adjacent to each other and are configured to form a channel 724.

Enclosed within the top inner wall 718 is a single-axle DC motor 726 having a planetary gearbox 728, on which is mounted a hypoid gear 730. Also enclosed within the top inner walls 718 are a pair of wheels 732 and 734, with wheel 732 having a surface thereon to engage the hypoid gear 730. When energized by motor 726, hypoid gear 730 engages the surface on wheel 732 causing a rotational movement of the wheel 732, which also results in the rotation of wheel 734.

Enclosed within the bottom inner wall 720 is a single-axle DC motor 738 having a planetary gearbox 740, on which is mounted a hypoid gear 744. Also enclosed within the bottom inner walls 720 are a pair of wheels 746 and 748, with wheel 746 having a surface thereon a surface to engage the hypoid gear 744. When energized by motor 738, hypoid gear 744 engages the surface on wheel 746 causing a rotational movement of the wheel 746, which also results in the rotation of wheel 748.

The single-axle DC motor 726 causes the wheels 732, 734 to move rotationally in a first direction, resulting in a first inversion of the top inner device surface 708 and the top outer device surface 710, and the single-axle DC motor 738 causes the wheels 746, 748 to move rotationally in a second direction, resulting in a second inversion of the bottom inner device surface 714 and the bottom outer device surface 712, where the first direction is opposite that of the second direction. The first and second inversions safely propel the device 700 without sliding of the top and bottom outer device surfaces 710, 712 against any contacted external wall and allowing low friction movement of the device.

FIG. 8a depicts another configuration that utilizes a bevel gear in a toroidal vehicle. This configuration allows the motor's axle to spin at the level of the wheel's axle and provides a step-down in rotational output.

FIG. 8b depicts an embodiment of a toroidal vehicle having a bevel gear in a top portion of the toroidal vehicle and having another bevel gear in a bottom portion of the toroidal vehicle. In the embodiment depicted in FIG. 8b, the present invention provides a toroidal device 800 having a top portion 802 and a bottom portion 804 that are symmetric about a central axis 806, where the top portion 802 has a top inner device surface 808 and a top outer device surface 810 and the bottom portion 804 has a bottom inner device surface 814 and a bottom outer device surface 812, each of the top inner device surface 808 and top outer device surface 810 having a top inner wall 818 and a top outer wall 816 and each of the bottom inner device surface 814 and bottom outer device surface 812 comprising a bottom inner wall 820 and a bottom outer wall 822, where a portion of the top outer wall 816 associated with the top inner device surface 808 and another portion of the bottom outer wall 822 associated with the bottom inner device surface 814 are adjacent to each other and are configured to form a channel 824.

Enclosed within the top inner wall 818 is a single-axle DC motor 826 having a planetary gearbox 828, on which is mounted a bevel gear 830. Also enclosed within the top inner walls 818 are a pair of wheels 832 and 834, with wheel 832 having a surface thereon to engage the bevel gear 830. When energized by motor 826, bevel gear 830 engages the surface on wheel 832 causing a rotational movement of the wheel 832, which also results in the rotation of wheel 834.

Enclosed within the bottom inner wall 820 is a single-axle DC motor 838 having a planetary gearbox 840, on which is mounted a bevel gear 844. Also enclosed within the bottom inner walls 820 are a pair of wheels 846 and 848, with wheel 846 having a surface thereon a surface to engage the bevel gear 844. When energized by motor 838, bevel gear 844 engages the surface on wheel 846 causing a rotational movement of the wheel 846, which also results in the rotation of wheel 848.

The single-axle DC motor 826 causes the wheels 832, 834 to move rotationally in a first direction, resulting in a first inversion of the top inner device surface 808 and the top outer device surface 810, and the single-axle DC motor 838 causes the wheels 846, 848 to move rotationally in a second direction, resulting in a second inversion of the bottom inner device surface 814 and the bottom outer device surface 812, where the first direction is opposite that of the second direction. The first and second inversions safely propel the device 800 without sliding of the top and bottom outer device surfaces 810, 812 against any contacted external wall and allowing low friction movement of the device.

It should be noted that while the motors in the figures above have been shown with a planetary gear unit, the present invention does envision having motors without such planetary gear units. For example, FIG. 9a depicts a bevel gear configuration that shows the motor without the planetary step-down gears. This configuration allows the motor's axle to spin at the level of the wheel's axle and provides a step-down in rotational output. A simple arrangement without a planetary step-down can also be configured with both worm gears and hypoid gears.

FIG. 9*b* depicts an embodiment of a toroidal vehicle having a bevel gear in a top portion of the toroidal vehicle and having another bevel gear in a bottom portion of the toroidal vehicle. In the embodiment depicted in FIG. 9*b*, the present invention provides a toroidal device 900 having a top portion 902 and a bottom portion 904 that are symmetric about a central axis 906, where the top portion 902 has a top inner device surface 908 and a top outer device surface 910 and the bottom portion 904 has a bottom inner device surface 914 and a bottom outer device surface 912, each of the top inner device surface 908 and top outer device surface 910 having a top inner wall 918 and a top outer wall 916 and each of the bottom inner device surface 914 and bottom outer device surface 912 comprising a bottom inner wall 920 and a bottom outer wall 922, where a portion of the top outer wall 916 associated with the top inner device surface 908 and another portion of the bottom outer wall 922 associated with the bottom inner device surface 914 are adjacent to each other and are configured to form a channel 924.

Enclosed within the top inner wall 918 is a single-axle DC motor 926 on which is mounted a bevel gear 930. Also enclosed within the top inner walls 918 are a pair of wheels 932 and 934, with wheel 932 having a surface thereon to engage the bevel gear 930. When energized by motor 926, bevel gear 930 engages the surface on wheel 932 causing a rotational movement of the wheel 932, which also results in the rotation of wheel 934.

Enclosed within the bottom inner wall 920 is a single-axle DC motor 938 on which is mounted a bevel gear 944. Also enclosed within the bottom inner walls 920 are a pair of wheels 946 and 948, with wheel 946 having a surface thereon a surface to engage the bevel gear 944. When energized by motor 938, bevel gear 944 engages the surface on wheel 946 causing a rotational movement of the wheel 946, which also results in the rotation of wheel 948.

The single-axle DC motor 926 causes the wheels 932, 934 to move rotationally in a first direction, resulting in a first inversion of the top inner device surface 908 and the top outer device surface 910, and the single-axle DC motor 938 causes the wheels 946, 948 to move rotationally in a second direction, resulting in a second inversion of the bottom inner device surface 914 and the bottom outer device surface 912, where the first direction is opposite that of the second direction. The first and second inversions safely propel the device 900 without sliding of the top and bottom outer device surfaces 910, 912 against any contacted external wall and allowing low friction movement of the device.

The toroidal vehicle can be constructed with one or more motor/drivetrains systems on one or more wheels. FIG. 10 depicts a single drivetrain system.

Another novel drivetrain system has the benefit of rotating multiple wheels on the vehicle's front and/or back wheels at the same rate. This step-down gear involves a novel configuration hereby referred to as an internal curved spiral (ICS)/internal spur (IS) gear. The present invention's ICS/IS gear is depicted in FIGS. 11*a-c*. The present invention's ICS/IS gear comprises two components: the internal curved spiral (ICS) gear component 1102 which is depicted in FIG. 11*a* and the internal spur (IS) gear component 1104 which is depicted in FIG. 11*b*: The materials used in the construction of ICS gear component 1102 or IS gear component 1104 (or other gear components discussed below) may be the metal alloys or plastics or other materials appropriate for gears of similar size and function. The particular type of material used to construct such gear components should not be used to limit the scope of the present invention. The IS gear 1104 is then permanently attached to or constructed on bloc (with 3D printing or machining) with the ICS gear 1102 to form a single unit 1106 as shown in FIG. 11*c*. if constructed separately, the components 1102 and 1104 may be attached by adhesive bonding, chemical bonding or metallic bonding, depending upon the material used in construction of the gears. However, the particular manner in which such components are attached should not be used to limit the present invention. It should be noted that throughout the specification, while the ICS gear and IS gear are described as separate units, a single unit may be manufactured that is shaped like what is shown in FIG. 11*c*. Such single units are within the scope of the present invention.

FIG. 11*d* is a cross section of the ICS gear depicted in FIG. 11*a*. Note the curve in the ICS aspect as depicted in FIG. 11*d* matches the curve of the vehicle's wheel (which itself may be a spur gear). FIG. 11*e* is a cross-section of the IS gear depicted in FIG. 11*b*. FIG. 11*f* is a cross-section of the ICS/IS gear combination depicted in FIG. 11*c*. The two-dimensional representation of the ICS/IS gear as depicted in FIG. 11*f* will be seen in the representations of the toroidal vehicle in subsequent figures described below.

As depicted in FIG. 12*a*, a simple spur gear 1202 is located on the motor's output axle, where the spur gear 1202 engages the IS gear of the combined ICS/IS gear unit 1106 shown in FIG. 11*c*. Spur gear 1202 spins (based on the energized motor) and rotates the IS gear. As depicted in FIG. 12*b*, wheels 1206 and 1208 that rotate the toroidal vehicle's tread may be configured as spur gears that fit against the inner curve of the ICS part of the ICS/IS gear unit 1106 of FIG. 11*c*. The rotation of the ICS/IS gear causes the spur wheels to rotate at a stepped-down rate as depicted in FIG. 12*b*.

While a single motor is depicted in FIG. 12*a*, a plurality of motors may be used as depicted in FIG. 13*a-b*. This configuration results in a step-down in rotation of the internal spur gear. The curved spiral aspect of the ICS/IS gear combination gear meshes with the wheels 1306 and 1308 of the vehicle that are configured to be spur gears as shown in FIG. 13*a*. The rotation of the wheel is driven by the rotation of the ICS/IS gear, resulting in yet another step-down. FIG. 13*b* depicts two motors 1308 and 1310 that engage the IS gear. Each of motors 1308 or 1310 may additionally comprise planetary gears 1312 or 1314. The use of planetary gears may be necessary in the motor's rotational speed is too great and the rotating wheels that turn the tread spin too quickly despite the step-down provided by the ICS/IS gear. The configuration of this novel gear allows the synchronization of all wheels at one end (or both ends if a dual axle system is used) while having a low profile and allowing rotation of the toroidal tread through the vehicle.

FIG. 14*a* depicts a cross-section of one embodiment of the present invention's vehicle where a relatively slower motor speed may allow a DC motor to be directly coupled to an ICS/IS gear (without planetary gear) in the toroidal vehicle. The components of the drivetrain including 1458, 1454, 1456, 1452, 1448, 1446, 1444 may be constructed from standard materials used in the construction similarly-sized gears such as plastic and metal. The grey arrows in the figures such as FIG. 14*a* are a 2-dimensional representation of the rotating ICS/IS gear in a plane perpendicular with the diagram. For the purpose of simplicity, many of the figures, e.g., FIG. 14*a*, do not depict the cylindrical frame to which internal components are attached. The previously depicted and described frame is included in all such embodiments of the toroidal device and is merely excluded from these figures for better illustrating other components of the present invention. In the embodiment depicted in FIG. 14*a*, the present invention's device comprises a toroidal device 1400 having a top portion 1402 and a bottom portion 1404 that are symmetric about a central axis 1406, the top portion 1402 having a top inner device surface 1408 and a top outer device surface 1410 and the bottom portion 1404 having a bottom inner device surface 1414 and a bottom outer device surface 1412, each of the top inner device surface 1408 and top outer device surface 1410 having a top inner wall 1418 and a top outer wall 1416 and each of the bottom inner device surface 1414 and bottom outer device surface 1412 comprising a bottom inner wall 1420 and a bottom outer wall 1422, where a portion of the top outer wall 1416 associated with the top inner device surface 1408 and another portion of the bottom outer wall 1422 associated with the bottom inner device surface 1414 are adjacent to each other and are configured to form a channel 1424. Elements 1438 and 1440 are gears similar to the described ICS/IS gear 1428, 1430. Note that FIG. 11*f*'s, elements 1430/1428 are 2 dimensional representations of FIG. 11*c*.

The top portion 1402 comprises the following components enclosed within the top inner wall 1418: (i) a top geared wheel 1426; (ii) a top internal curved spiral (ICS) gear 1428 configured to engage the top geared wheel 1426; (iii) a top internal spur (IS) gear 1430 coupled to the top ICS gear 1428; and (iv) a top direct current (DC) motor 1432 having a top spur gear 1434 at one end that is configured to engage the top IS gear 1430 and an engagement mechanism 1438, 1440 at another, opposite end that is configured to engage a top non-geared wheel 1442.

The bottom portion 1404 comprises the following components enclosed within the bottom inner wall 1420: (i) a bottom geared wheel 1444; (ii) a bottom ICS gear 1446 configured to engage the bottom geared wheel 1444; (iii) a bottom IS gear 1448 coupled to the bottom ICS gear 1446; and (iv) a bottom DC motor 1450 having a bottom spur gear 1452 at one end that is configured to engage the bottom IS gear 1448 and another engagement mechanism 1454, 1456 at another, opposite end that is configured to engage a bottom non-geared wheel 1458. Elements 1454 is the same gear as 1438, and 1456 is the same structure as 1440. Since elements 1438 and 1454 are 2-dimensional transverse section of the same circular gear, they appear as separate entities but in fact are different sections of the same gear.

The top ICS gear 1428 and the bottom ICS gear 1446 are part of a single ICS gear confined within the toroidal device 1400 and the top IS gear 1430 and bottom IS gear 1448 are part of a single IS gear within the toroidal device 1400.

The top DC motor 1432 is configured to rotate the top spur gear 1434 that engages the top IS gear 1430 coupled to the top ICS gear 1428 to cause the top geared wheel 1426 to move rotationally in a first direction 1460, resulting in a first inversion of the top inner device surface 1408 and the top outer device surface 1410 and, at the same time, the bottom DC motor 1450 is configured to rotate the bottom spur gear 1452 that engages the bottom IS gear 1448 coupled to the bottom ICS gear 1446 to cause the bottom geared wheel 1444 to move rotationally in a second direction 1462, resulting in a second inversion of the bottom inner device surface 1414 and the bottom outer device surface 1412, where the first direction 1460 is opposite that of the second direction 1462. The first and second inversions safely propel the device 1400 without sliding of the top and bottom outer device surfaces 1410, 1412 against any contacted external wall and allowing low friction movement of the device.

FIG. 14*b* depicts an extension of the embodiment depicted in FIG. 14*a*, with the inclusion of planetary gears 1464 and 1466, used in conjunction with each of the previously described motors 1432 and 1450, respectively. Other than planetary gears 1464 and 1466, FIG. 14*b* includes all other elements of previously described FIG. 14*a*. The benefit of adding the planetary gears 1464 and 1466 (in comparison to the embodiment shown in FIG. 14*a*) is that the planetary gears allow extra step-down within the driveshaft to allow a slower turning of the vehicle's wheels.

FIG. 15 depicts another embodiment of the present invention's toroidal device 1500 where two motors 1532, 1533 (without a planetary gearbox) are placed in a back-to-back configuration on the top portion 1502 and two motors 1550, 1551 (without a planetary gearbox) are placed in a back-to-back configuration on the bottom portion 1504 where the motors 1532, 1533, 1550, 1551 work in conjunction with a pair of ICS/IS gears 1528/1530, 1538/1540. With this configuration, either the back-facing motors need to change polarity or the direction of the spiral angle needs to be reversed. In other words, the direction of the threads of the ICS portion of the ICS/IS gear can be reversed (such as clockwise direction of torque on the front ICS/IS gear and anti-clockwise direction of torque) to allow all of the vehicle's wheels the rotate in the same direction, depending upon the rotational configuration of the motors.

In the embodiment depicted in FIG. 15, the present invention provides a toroidal device 1500 having a top portion 1502 and a bottom portion 1504 that are symmetric about a central axis 1506, where the top portion 1502 has a top inner device surface 1508 and a top outer device surface 1510 and the bottom portion 1504 has a bottom inner device surface 1514 and a bottom outer device surface 1512, each of the top inner device surface 1508 and top outer device surface 1510 having a top inner wall 1518 and a top outer wall 1516 and each of the bottom inner device surface 1514 and bottom outer device surface 1512 comprising a bottom inner wall 1520 and a bottom outer wall 1522, where a portion of the top outer wall 1516 associated with the top inner device surface 1508 and another portion of the bottom outer wall 1522 associated with the bottom inner device surface 1514 are adjacent to each other and are configured to form a channel 1524.

The top portion 1502 comprising the following components enclosed within the top inner wall 1518: (i) a first top geared wheel 1526; (ii) a second top geared wheel 1542; (iii) a first top internal curved spiral (ICS) gear 1528 configured to engage the first top geared wheel 1526; (iv) a first top internal spur (IS) gear 1530 coupled to the first top ICS gear 1528; (v) a first top DC motor 1532 having a first top spur gear 1534 at one end that is configured to engage the first top IS gear 1530; (vi) a second top DC motor 1533 that abuts the first top DC motor 1532 at one end and having a second top spur gear 1535 at another end; (vii) a second top IS gear 1540 configured to engage the second top spur gear 1535; and (viii) a second top ICS gear 1538 coupled to the second top IS gear 1540 and configured to engage the second top geared wheel 1542.

The bottom portion 1504 comprising the following components enclosed within the bottom inner wall 1520: (i) a first bottom geared wheel 1544; (ii) a second bottom geared wheel 1548; (iii) a first bottom ICS gear 1546 configured to engage the first bottom geared wheel 1544; (iv) a first bottom IS gear 1548 coupled to the first bottom ICS gear 1546; (v) a first bottom DC motor 1550 having a first bottom spur gear 1552 at one end that is configured to engage the first bottom IS gear 1548; (vi) a second bottom DC motor 1551 that abuts the first bottom DC motor 1550 at one end and having a second bottom spur gear 1553 at another end; (vii) a second bottom IS gear 1556 configured to engage the second bottom spur gear 1553; and (viii) a second bottom ICS gear 1554 coupled to the second bottom IS gear 1556 and configured to engage the second bottom geared wheel 1548.

The first top ICS gear 1528 and the first bottom ICS gear 1546 are part of a single first ICS gear confined within the toroidal device 1500 and the first top IS gear 1530 and first bottom IS gear 1548 are part of a single first IS gear within the toroidal device 1500.

The second top ICS gear 1538 and the second bottom ICS gear 1554 are part of a single second ICS gear confined within the toroidal device 1500 and the second top IS gear 1540 and second bottom IS gear 1556 are part of a single second IS gear within the toroidal device 1500.

The first top DC motor 1532 is configured to rotate the first top spur gear 1534 that engages the first top IS gear 1530 coupled to the first top ICS gear 1528 to cause the first top geared wheel 1526 to move rotationally in a first direction 1560, and the second top DC motor 1533 is configured to rotate the second top spur gear 1535 that engages the second top IS gear 1540 coupled to the second top ICS gear 1538 to cause the second top geared wheel 1542 to move rotationally in the first direction 1560, resulting in a first inversion of the top inner device surface 1508 and the top outer device surface 1510.

The first bottom DC motor 1550 configured to rotate the first bottom spur gear 1552 that engages the first bottom IS gear 1548 coupled to the first bottom ICS gear 1546 to cause the first bottom geared wheel 1544 to move rotationally in a second direction 1562, and the second bottom DC motor 1551 configured to rotate the second bottom spur gear 1553 that engages the second bottom IS gear 1556 coupled to the second bottom ICS gear 1554 to cause the second bottom geared wheel 1548 to move rotationally in the second direction 1562, resulting in a second inversion of the bottom inner device surface 1514 and the bottom outer device surface 1512, the first direction 1560 opposite that of the second direction 1562, the first and second inversions safely propelling the device 1500 without sliding of the top and bottom outer device surfaces 1510, 1512 against any contacted external wall and allowing low friction movement of the device.

It is noteworthy that in the above configurations, a single-axle motor is used. However, a double-axle motor as depicted in FIGS. 16*a-c* may also be used in all configurations by using an equivalent drivetrain from each axle. FIG. 16*a* depicts a double-axle motor. FIG. 16*b* depicts the double-axle motor of FIG. 16*a* equipped with a planetary gearbox at each axle. FIG. 16*c* depicts the double-axle motor of FIG. 16*b* with the pair of planetary gearboxes along with a pair of spur gears.

FIG. 17*a* depicts a double-axle motor with a pair of planetary gearboxes on either side, along with a worm gear mounted on either side of the motor. Each worm gear engages a gear wheel as shown to cause movement of the toroidal balloon.

FIG. 17*b* depicts an embodiment of a toroidal vehicle having two such worm gears in a top portion of the toroidal vehicle and having two such worm gears in a bottom portion of the toroidal vehicle. In the embodiment depicted in FIG. 17*b*, the present invention provides a toroidal device 1700 having a top portion 1702 and a bottom portion 1704 that are symmetric about a central axis 1706, where the top portion 1702 has a top inner device surface 1708 and a top outer device surface 1710 and the bottom portion 1704 has a bottom inner device surface 1714 and a bottom outer device surface 1712, each of the top inner device surface 1708 and top outer device surface 1710 having a top inner wall 1718 and a top outer wall 1716 and each of the bottom inner device surface 1714 and bottom outer device surface 1712 comprising a bottom inner wall 1720 and a bottom outer wall 1722, where a portion of the top outer wall 1716 associated with the top inner device surface 1708 and another portion of the bottom outer wall 1722 associated with the bottom inner device surface 1714 are adjacent to each other and are configured to form a channel 1724.

Enclosed within the top inner wall 1718 is a double-axle DC motor 1726, which is flanked on either side by a pair of planetary gearboxes 1728, 1730, on which are mounted a pair of worm gears 1732 and 1738. Also, enclosed within the top inner walls 1718 are a pair of wheels 1734 and 1740, each of which has a gear wheel 1736, 1742 mounted thereon. When energized by motor 1726, worm gear 1732 engages the gears on the gear wheel 1736 causing a rotational movement, which then rotates the wheel 1734. Similarly, when energized by motor 1726, worm gear 1738 engages the gears on the gear wheel 1742 causing a rotational movement, which then rotates the wheel 1740.

Enclosed within the bottom inner wall 1720 is a double-axle DC motor 1744, which is flanked on either side by a pair of planetary gearboxes 1746, 1748, on which are mounted a pair of worm gears 1750 and 1756. Also, enclosed within the bottom inner walls 1720 are a pair of wheels 1752 and 1760, each of which has a gear wheel 1754, 1758 mounted thereon. When energized by motor 1744, worm gear 1750 engages the gears on the gear wheel 1754 causing a rotational movement, which then rotates the wheel 1752. Similarly, when energized by motor 1744, worm gear 1756 engages the gears on the gear wheel 1758 causing a rotational movement, which then rotates the wheel 1760.

The double-axle DC motor 1726 causes the wheels 1734, 1740 to move rotationally in a first direction, resulting in a first inversion of the top inner device surface 1708 and the top outer device surface 1710, and the double-axle DC motor 1744 causes the wheels 1752, 1760 to move rotationally in a second direction, resulting in a second inversion of the bottom inner device surface 1714 and the bottom outer device surface 1712, where the first direction is opposite that of the second direction. The first and second inversions safely propel the device 1700 without sliding of the top and bottom outer device surfaces 1710, 1712 against any contacted external wall and allowing low friction movement of the device.

It should be noted that while a worm gear is shown in FIG. 17*b*, other gears, such as a hypoid gear, may also be used. Such an example is depicted in FIGS. 18*a-b*.

FIG. 18*a* depicts a double-axle motor with a pair of planetary gearboxes on either side, along with a hypoid gear mounted on either side of the motor. Each hypoid gear engages a surface on a wheel to cause movement of the toroidal balloon.

FIG. 18*b* depicts an embodiment of a toroidal vehicle having two such hypoid gears in a top portion of the toroidal vehicle and having two such hypoid gears in a bottom portion of the toroidal vehicle. In the embodiment depicted in FIG. 18*b*, the present invention provides a toroidal device 1800 having a top portion 1802 and a bottom portion 1804 that are symmetric about a central axis 1806, where the top portion 1802 has a top inner device surface 1808 and a top outer device surface 1810 and the bottom portion 1804 has a bottom inner device surface 1814 and a bottom outer device surface 1812, each of the top inner device surface 1808 and top outer device surface 1810 having a top inner wall 1818 and a top outer wall 1816 and each of the bottom inner device surface 1814 and bottom outer device surface 1812 comprising a bottom inner wall 1820 and a bottom outer wall 1822, where a portion of the top outer wall 1816 associated with the top inner device surface 1808 and another portion of the bottom outer wall 1822 associated with the bottom inner device surface 1814 are adjacent to each other and are configured to form a channel 1824.

Enclosed within the top inner wall 1818 is a double-axle DC motor 1826, which is flanked on either side by a pair of planetary gearboxes 1828, 1830, on which are mounted a pair of hypoid gears 1832 and 1838. Also enclosed within the top inner walls 1818 are a pair of wheels 1834 and 1842, each of which has thereon a surface to engage the associated hypoid gear (i.e., hypoid gear 1832 or hypoid gear 1838). When energized by motor 1826, hypoid gear 1832 engages the surface on the wheel 1834 causing a rotational movement of the wheel 1834. Similarly, when energized by motor 1826, hypoid gear 1838 engages the surface on the wheel 1842 causing a rotational movement of the wheel 1842.

Enclosed within the bottom inner wall 1820 is a double-axle DC motor 1844, which is flanked on either side by a pair of planetary gearboxes 1846, 1848, on which are mounted a pair of hypoid gears 1850 and 1858. Also enclosed within the bottom inner walls 1820 are a pair of wheels 1852 and 1860, each of which has thereon a surface to engage the associated hypoid gear (i.e., hypoid gear 1850 or hypoid gear 1858). When energized by motor 1844, hypoid gear 1850 engages the surface on the wheel 1852 causing a rotational movement of the wheel 1852. Similarly, when energized by motor 1844, hypoid gear 1858 engages the surface on the wheel 1860 causing a rotational movement of the wheel 1860.

The double-axle DC motor 1826 causes the wheels 1834, 1842 to move rotationally in a first direction, resulting in a first inversion of the top inner device surface 1808 and the top outer device surface 1810, and the double-axle DC motor 1844 causes the wheels 1852, 1860 to move rotationally in a second direction, resulting in a second inversion of the bottom inner device surface 1814 and the bottom outer device surface 1812, where the first direction is opposite that of the second direction. The first and second inversions safely propel the device 1800 without sliding of the top and bottom outer device surfaces 1810, 1812 against any contacted external wall and allowing low friction movement of the device.

In FIG. 18*b*, the surface on the wheel 1834 that engages the hypoid gear 1832 is shown in the front side of the wheel 1834, but the surface on the wheel 1842 that engages the hypoid gear 1838 is shown on the back side of the wheel 1842. Also, in FIG. 18*b*, the surface on the wheel 1860 that engages the hypoid gear 1858 is shown in the front side of the wheel 1860, but the surface on the wheel 1852 that engages the hypoid gear 1850 is shown on the back side of the wheel 1852.

FIG. 19*a* depicts a double-axle motor with a pair of planetary gearboxes on either side, along with a bevel gear mounted on either side of the motor. Each bevel gear engages a surface on a wheel to cause movement of the toroidal balloon.

FIG. 19*b* depicts an embodiment of a toroidal vehicle having two such bevel gears in a top portion of the toroidal vehicle and having two such bevel gears in a bottom portion of the toroidal vehicle. In the embodiment depicted in FIG. 19*b*, the present invention provides a toroidal device 1900 having a top portion 1902 and a bottom portion 1904 that are symmetric about a central axis 1906, where the top portion 1902 has a top inner device surface 1908 and a top outer device surface 1910 and the bottom portion 1904 has a bottom inner device surface 1914 and a bottom outer device surface 1912, each of the top inner device surface 1908 and top outer device surface 1910 having a top inner wall 1918 and a top outer wall 1916 and each of the bottom inner device surface 1914 and bottom outer device surface 1912 comprising a bottom inner wall 1920 and a bottom outer wall 1922, where a portion of the top outer wall 1916 associated with the top inner device surface 1908 and another portion of the bottom outer wall 1922 associated with the bottom inner device surface 1914 are adjacent to each other and are configured to form a channel 1924.

Enclosed within the top inner wall 1918 is a double-axle DC motor 1926, which is flanked on either side by a pair of planetary gearboxes 1928, 1930, on which are mounted a pair of bevel gears 1932 and 1938. Also enclosed within the top inner walls 1918 are a pair of wheels 1934 and 1942, each of which has thereon a surface to engage the associated bevel gear (i.e., bevel gear 1932 or bevel gear 1938). When energized by motor 1926, bevel gear 1932 engages the surface on the wheel 1934 causing a rotational movement of the wheel 1934. Similarly, when energized by motor 1926, bevel gear 1938 engages the surface on the wheel 1942 causing a rotational movement of the wheel 1942.

Enclosed within the bottom inner wall 1920 is a double-axle DC motor 1944, which is flanked on either side by a pair of planetary gearboxes 1946, 1948, on which are mounted a pair of bevel gears 1950 and 1958. Also enclosed within the bottom inner walls 1920 are a pair of wheels 1952 and 1960, each of which has thereon a surface to engage the associated bevel gear (i.e., bevel gear 1950 or bevel gear 1958). When energized by motor 1944, bevel gear 1950 engages the surface on the wheel 1952 causing a rotational movement of the wheel 1952. Similarly, when energized by motor 1944, bevel gear 1958 engages the surface on the wheel 1960 causing a rotational movement of the wheel 1960.

The double-axle DC motor 1926 causes the wheels 1934, 1942 to move rotationally in a first direction, resulting in a first inversion of the top inner device surface 1908 and the top outer device surface 1910, and the double-axle DC motor 1944 causes the wheels 1952, 1960 to move rotationally in a second direction, resulting in a second inversion of the bottom inner device surface 1914 and the bottom outer device surface 1912, where the first direction is opposite that of the second direction. The first and second inversions safely propel the device 1900 without sliding of the top and bottom outer device surfaces 1910, 1912 against any contacted external wall and allowing low friction movement of the device.

In FIG. 19*b*, the surface on the wheel 1934 that engages the bevel gear 1932 is shown in the front side of the wheel 1934, but the surface on the wheel 1942 that engages the bevel gear 1938 is shown on the back side of the wheel 1942. Also, in FIG. 19*b*, the surface on the wheel 1960 that engages the bevel gear 1958 is shown in the front side of the wheel 1960, but the surface on the wheel 1952 that engages the bevel gear 1950 is shown on the back side of the wheel 1952.

While the double-axle motors are shown with planetary gearboxes in FIG. 18*b* and FIG. 19*b*, such double-axle motors can also be used without planetary gearboxes. Such examples are depicted in FIGS. 20*a-c*. FIG. 20*a* depicts a double-axle motor with a worm gear on either side. FIG. 20*b* depicts a double-axle motor with a hypoid gear on either side. FIG. 20*c* depicts a double-axle motor with a bevel gear on either side.

FIG. 21a depicts a double-axle motor with a pair of hypoid gears mounted on either side of the motor. Each hypoid gear engages a surface on a wheel to cause movement of the toroidal balloon. It is noteworthy that any of the double-axle systems without planetary gearboxes shown in FIG. 20a and FIG. 20c can be used in a configuration similar to FIG. 21a.

FIG. 21b depicts an embodiment of a toroidal vehicle without planetary gears having two such hypoid gears in a top portion of the toroidal vehicle and having two such hypoid gears in a bottom portion of the toroidal vehicle. In the embodiment depicted in FIG. 21b, the present invention provides a toroidal device 2100 having a top portion 2102 and a bottom portion 2104 that are symmetric about a central axis 2106, where the top portion 2102 has a top inner device surface 2108 and a top outer device surface 2110 and the bottom portion 2104 has a bottom inner device surface 2114 and a bottom outer device surface 2112, each of the top inner device surface 2108 and top outer device surface 2110 having a top inner wall 2118 and a top outer wall 2116 and each of the bottom inner device surface 2114 and bottom outer device surface 2112 comprising a bottom inner wall 2120 and a bottom outer wall 2122, where a portion of the top outer wall 2116 associated with the top inner device surface 2108 and another portion of the bottom outer wall 2122 associated with the bottom inner device surface 2114 are adjacent to each other and are configured to form a channel 2124.

Enclosed within the top inner wall 2118 is a double-axle DC motor 2126, which is flanked on either side by a pair of hypoid gears 2132 and 2138. Also enclosed within the top inner walls 2118 are a pair of wheels 2134 and 2142, each of which has thereon a surface to engage the associated hypoid gear (i.e., hypoid gear 2132 or hypoid gear 2138). When energized by motor 2126, hypoid gear 2132 engages the surface on the wheel 2134 causing a rotational movement of the wheel 2134. Similarly, when energized by motor 2126, hypoid gear 2138 engages the surface on the wheel 2142 causing a rotational movement of the wheel 2142.

Enclosed within the bottom inner wall 2120 is a double-axle DC motor 2144, which is flanked on either side by a pair of hypoid gears 2150 and 2158. Also enclosed within the bottom inner walls 2120 are a pair of wheels 2152 and 2160, each of which has thereon a surface to engage the associated hypoid gear (i.e., hypoid gear 2150 or hypoid gear 2158). When energized by motor 2144, hypoid gear 2150 engages the surface on the wheel 2152 causing a rotational movement of the wheel 2152. Similarly, when energized by motor 2144, hypoid gear 2158 engages the surface on the wheel 2160 causing a rotational movement of the wheel 2160.

The double-axle DC motor 2126 causes the wheels 2134, 2142 to move rotationally in a first direction, resulting in a first inversion of the top inner device surface 2108 and the top outer device surface 2110, and the double-axle DC motor 2144 causes the wheels 2152, 2160 to move rotationally in a second direction, resulting in a second inversion of the bottom inner device surface 2114 and the bottom outer device surface 2112, where the first direction is opposite that of the second direction. The first and second inversions safely propel the device 2100 without sliding of the top and bottom outer device surfaces 2110, 2112 against any contacted external wall and allowing low friction movement of the device.

In FIG. 21b, the surface on the wheel 2134 that engages the hypoid gear 2132 is shown in the front side of the wheel 2134, but the surface on the wheel 2142 that engages the hypoid gear 2138 is shown on the back side of the wheel 2142. Also, in FIG. 21b, the surface on the wheel 2160 that engages the hypoid gear 2158 is shown in the front side of the wheel 2160, but the surface on the wheel 2152 that engages the hypoid gear 2150 is shown on the back side of the wheel 2152.

FIG. 22 depicts a double-axle motor without planetary gearboxes and an ICS/IS gear driving both front and rear wheels. In this configuration, all wheels, both front and back, move in synchrony which may optimize the rotation of the toroidal tread. It is noteworthy that this double-axle ICS/IS gear drive can exist also with planetary gearboxes on all axles. FIG. 22 depicts an embodiment of a toroidal vehicle without planetary gears having two spur gears in a top portion of the toroidal vehicle and having two spur gears in a bottom portion of the toroidal vehicle. In the embodiment depicted in FIG. 22, the present invention provides a toroidal device 2200 having a top portion 2202 and a bottom portion 2204 that are symmetric about a central axis 2206, where the top portion 2202 has a top inner device surface 2208 and a top outer device surface 2210 and the bottom portion 2204 has a bottom inner device surface 2214 and a bottom outer device surface 2212, each of the top inner device surface 2208 and top outer device surface 2210 having a top inner wall 2218 and a top outer wall 2216 and each of the bottom inner device surface 2214 and bottom outer device surface 2212 comprising a bottom inner wall 2220 and a bottom outer wall 2222, where a portion of the top outer wall 2216 associated with the top inner device surface 2208 and another portion of the bottom outer wall 2222 associated with the bottom inner device surface 2214 are adjacent to each other and are configured to form a channel 2124.

The top portion 2202 comprises the following components enclosed within the top inner wall 2218: (i) a first top geared wheel 2226; (ii) a second top geared wheel 2228; (iii) a first top internal curved spiral (ICS) gear 2230 configured to engage the first top geared wheel 2226; (iv) a second top ICS gear 2232 configured to engage the second top geared wheel 2228; (v) a first top internal spur (IS) gear 2234 coupled to the first top ICS gear 2230; (vi) a second top IS gear 2236 coupled to the second top ICS gear 2232; and (vii) a top DC motor 2238 having a first top spur gear 2240 at one end and a second top spur gear 2242 at another, opposite end, wherein the first top spur gear 2240 is configured to engage the first top IS gear 2234 and the second top spur gear 2242 configured to engage the second top IS gear 2236.

The bottom portion 2204 comprises the following components enclosed within the bottom inner wall 2220: (i) a first bottom geared wheel 2244; (ii) a second bottom geared wheel 2246; (iii) a first bottom ICS gear 2248 configured to engage the first bottom geared wheel 2244; (iv) a second bottom ICS gear 2250 configured to engage the second bottom geared wheel 2246; (v) a first bottom IS gear 2252 coupled to the first bottom ICS gear 2248; (vi) a second bottom IS gear 2254 coupled to the second bottom ICS gear 2250; and (vii) a bottom DC motor 2256 having a first bottom spur gear 2258 at one end and a second bottom spur gear 2260 at another, opposite end, the first bottom spur gear 2258 configured to engage the first bottom IS gear 2252 and the second bottom spur gear 2260 configured to engage the second bottom IS gear 2254.

The first top ICS gear 2230 and the first bottom ICS gear 2248 are part of a single first ICS gear confined within the toroidal device 2200 and the first top IS gear 2234 and first bottom IS gear 2252 are part of a single first IS gear within the toroidal device.

The second top ICS gear 2232 and the second bottom ICS gear 2250 are part of a single second ICS gear confined within the toroidal device 2200 and the second top IS gear 2236 and second bottom IS gear 2254 are part of a single second IS gear within the toroidal device.

The top DC motor 2238 is configured to rotate the first top spur gear 2240 that engages the first top IS gear 2234 coupled to the first top ICS gear 2230 to cause the first top geared wheel 2226 to move rotationally in a first direction 2262, and the top DC motor 2238 is configured to rotate the second top spur gear 2242 that engages the second top IS gear 2236 coupled to the second top ICS gear 2232 to cause the second top geared wheel 2228 to move rotationally in the first direction 2262, resulting in a first inversion of the top inner device surface 2208 and the top outer device surface 2210.

The bottom DC motor 2256 is configured to rotate the first bottom spur gear 2258 that engages the first bottom IS gear 2252 coupled to the first bottom ICS gear 2248 to cause the first bottom geared wheel 2244 to move rotationally in a second direction 2264, and the bottom DC motor 2256 is configured to rotate the second bottom spur gear 2260 that engages the second bottom IS gear 2254 coupled to the second bottom ICS gear 2250 to cause the second bottom geared wheel 2246 to move rotationally in the second direction 2264, resulting in a second inversion of the bottom inner device surface 2214 and the bottom outer device surface 2212. The first direction 2262 is opposite that of the second direction 2264. The first and second inversions safely propel the device 2200 without sliding of the top and bottom outer device surfaces 2210 and 2212 against any contacted external wall and allowing low friction movement of the device.

It is also noteworthy that coreless motors are not the sole DC motor type to drive the vehicle.

In one embodiment, the toroidal device noted above is a toroidal balloon.

In one embodiment, the toroidal device further comprises a chamber to hold or release any one of, or a combination of, the following: compressed gas, liquid or solid.

In one embodiment, the toroidal device further comprises a location reporting system to report a location of the toroidal device.

In one embodiment, the toroidal device is initially positioned via any of the following: a probe, a scope, or a catheter.

In one embodiment, the toroidal device's top and bottom outer device surfaces and the toroidal device's top and bottom inner device surfaces are made from nylon.

In one embodiment, the toroidal device further comprises at least one light source and at least one camera disposed within either the top inner wall or the bottom inner wall.

In one embodiment, the top outer wall or bottom outer wall is coated with any of the following, or combinations thereof: a coagulogenic substance or an antimicrobial agent.

Conclusion

A system and method have been shown in the above embodiments for the effective implementation of drive trains for toroidal vehicles powered by direct-current motors. While various preferred embodiments have been shown and described, it will be understood that there is no intent to limit the invention by such disclosure, but rather, it is intended to cover all modifications falling within the spirit and scope of the invention, as defined in the appended claims.

What is claimed is:

1. A device comprising:
a toroidal device, the toroidal device comprising:

a toroid envelope having one continuous uninterrupted wall, the wall having an exterior surface facing an exterior of the toroidal device, and an interior surface facing an interior of the toroidal device;

a hole passing through the toroidal device along a central axis of the toroidal device, the exterior surface having an inner part facing the hole and radially toward the central axis and an outer part facing away from the hole and radially away from the central axis;

the toroidal device having a top portion and a bottom portion respectively above and below the central axis, respective portions of the inner part of the exterior surface in the top portion and the inner part of the exterior surface in the bottom portion being adjacent and cooperating to form a channel:

the top portion comprising, within the interior:
i. a top geared wheel;
ii. a top internal curved spiral (ICS) gear configured to engage the top geared wheel;
iii. a top internal spur (IS) gear coupled to the top ICS gear;
iv. a top direct current (DC) motor having a top spur gear at one end that is configured to engage the top IS gear and an engagement gear assembly at another, opposite end that is configured to engage a top non-geared wheel;

the bottom portion comprising, within the interior:
i. a bottom geared wheel;
ii. a bottom ICS gear configured to engage the bottom geared wheel;
iii. a bottom IS gear coupled to the bottom ICS gear;
iv. a bottom DC motor having a bottom spur gear at one end that is configured to engage the bottom IS gear and another engagement gear assembly at another, opposite end that is configured to engage a bottom non-geared wheel;

the top ICS gear and the bottom ICS gear are part of a single ICS gear confined within the toroidal device and the top IS gear and the bottom IS gear are part of a single IS gear within the toroidal device;

the top DC motor and the bottom DC motor are powered by at least one power source located within the toroidal device; and the top DC motor is configured to rotate the top spur gear that engages the top IS gear coupled to the top ICS gear to cause the top geared wheel to move rotationally in a first direction, resulting in a first inversion in the top portion such that at least a portion of the inner part of the exterior surface in the top portion becomes part of the outer part of the exterior surface in the top portion and at least a portion of the outer part of the exterior surface in the top portion becomes part of the inner part of the exterior surface in the top portion and, at the same time, the bottom DC motor is configured to rotate the bottom spur gear that engages the bottom IS gear coupled to the bottom ICS gear to cause the bottom geared wheel to move rotationally in a second direction, resulting in a second inversion in the bottom portion such that at least a portion of the inner part of the exterior surface in the bottom portion becomes part of the outer part of the exterior surface in the bottom portion and at least a portion of the outer part of the exterior surface in the bottom portion becomes part of the inner part of the exterior surface in the bottom portion, the first direction being opposite that of the second direction, the first and second inversions safely propelling the device without sliding of the outer part of the exterior surface in the top portion and the outer part of the exterior surface in the bottom portion against any contacted external wall and allowing low friction movement of the device.

2. The device as per claim 1, wherein the toroidal device is a toroidal balloon.

3. The device as per claim 1, wherein any one of the top DC motor or the bottom DC motor further comprises a set of planetary gears.

4. The device as per claim 1, wherein the device further comprises a chamber to hold or release any one of, or a combination of, the following: compressed gas, liquid or solid.

5. The device as per claim 1, further comprising a transmitter and an antenna configured to transmit a signal receivable by an external receiver to enable determination of a location of the device.

6. The device as per claim 1, wherein the device is configured to be positioned via a probe, a scope, or a catheter.

7. The device as per claim 1, wherein the wall is made from nylon.

8. The device as per claim 1, wherein the device further comprises at least one light source and at least one camera disposed within the interior in the top portion or the bottom portion.

9. The device as per claim 1, wherein the outer part of the exterior surface in the top portion or the outer part of the exterior surface in the bottom portion is coated with a coagulogenic substance, an antimicrobial agent, or a combination thereof.

10. A device comprising:

a toroidal device, the toroidal device comprising:

a toroid envelope having one continuous uninterrupted wall, the wall having an exterior surface facing an exterior of the toroidal device, and an interior surface facing an interior of the toroidal device;

a hole passing through the toroidal device along a central axis of the toroidal device, the exterior surface having an inner part facing the hole and radially toward the central axis and an outer part facing away from the hole and radially away from the central axis;

the toroidal device having a top portion and a bottom portion respectively above and below the central axis, respective portions of the inner part of the exterior surface in the top portion and the inner part of the exterior surface in the bottom portion being adjacent and cooperating to form a channel;

the top portion comprising, within the interior:

i. a first top geared wheel;

ii. a second top geared wheel;

iii. a first top internal curved spiral (ICS) gear configured to engage the first top geared wheel;

iv. a first top internal spur (IS) gear coupled to the first top ICS gear;

v. a first top DC motor having a first top spur gear at one end that is configured to engage the first top IS gear;

vi. a second top DC motor that abuts the first top DC motor at one end and has a second top spur gear at another end;

vii. a second top IS gear configured to engage the second top spur gear; and viii. a second top ICS gear coupled to the second top IS gear and configured to engage the second top geared wheel; and the bottom portion comprising, within the interior:

i. a first bottom geared wheel;

ii. a second bottom geared wheel;

iii. a first bottom ICS gear configured to engage the first bottom geared wheel;

iv. a first bottom IS gear coupled to the first bottom ICS gear;

v. a first bottom DC motor having a first bottom spur gear at one end that is configured to engage the first bottom IS gear;

vi. a second bottom DC motor that abuts the first bottom DC motor at one end and has a second bottom spur gear at another end;

vii. a second bottom IS gear configured to engage the second bottom spur gear; and viii. a second bottom ICS gear coupled to the second bottom IS gear and configured to engage the second bottom geared wheel;

the first top ICS gear and the first bottom ICS gear are part of a single first ICS gear confined within the toroidal device and the first top IS gear and the first bottom IS gear are part of a single first IS gear within the toroidal device;

the second top ICS gear and the second bottom ICS gear are part of a single second ICS gear confined within the toroidal device and the second top IS gear and the second bottom IS gear are part of a single second IS gear within the toroidal device;

the first top DC motor, the second top DC motor, the first bottom DC motor, and the second bottom DC motor are powered by at least one power source located within the toroidal device; and the first top DC motor is configured to rotate the first top spur gear that engages the first top IS gear coupled to the first top ICS gear to cause the first top geared wheel to move rotationally in a first direction, and the second top DC motor is configured to rotate the second top spur gear that engages the second top IS gear coupled to the second top ICS gear to cause the second top geared wheel to move rotationally in the first direction, resulting in a first inversion in the top portion such that at least a portion of the inner part of the exterior surface in the top portion becomes part of the outer part of the exterior surface in the top portion and at least a portion of the outer part of the exterior surface in the top portion becomes part of the inner part of the exterior surface in the top portion and, at the same time, the first bottom DC motor is configured to rotate the first bottom spur gear that engages the first bottom IS gear coupled to the first bottom ICS gear to cause the first bottom geared wheel to move rotationally in a second direction, and the second bottom DC motor is configured to rotate the second bottom spur gear that engages the second bottom IS gear coupled to the second bottom ICS gear to cause the second bottom geared wheel to move rotationally in the second direction, resulting in a second inversion in the bottom portion such that at least a portion of the inner part of the exterior surface in the bottom portion becomes part of the outer part of the exterior surface in the bottom portion and at least a portion of the outer part of the exterior surface in the bottom portion becomes part of the inner part of the exterior surface in the bottom portion, the first direction being opposite that of the second direction, the first and second inversions safely propelling the device without sliding of the outer part of the exterior surface in the top portion and the outer part of the exterior surface in the bottom portion against any contacted external wall and allowing low friction movement of the device.

11. The device as per claim 10, wherein the toroidal device is a toroidal balloon.

12. The device as per claim 10, wherein any one of the first top DC motor, the second top DC motor, the first bottom DC motor, or the second bottom DC motor further comprises a set of planetary gears.

13. The device as per claim 10, wherein the device further comprises a chamber to hold or release any one of, or a combination of, the following: compressed gas, liquid or solid.

14. The device as per claim 10, further comprising a transmitter and an antenna configured to transmit a signal receivable by an external receiver to enable determination of a location of the device.

15. The device as per claim 10, wherein the device is configured to be positioned via a probe, a scope, or a catheter.

16. The device as per claim 10, wherein the wall is made from nylon.

17. The device as per claim 10, wherein the device further comprises at least one light source and at least one camera disposed within the interior in the top portion or the bottom portion.

18. The device as per claim 10, wherein the outer part of the exterior surface in the top portion or the outer part of the exterior surface in the bottom portion is coated with a coagulogenic substance, an antimicrobial agent, or a combination thereof.

19. A device comprising:

a toroidal device, the toroidal device comprising:

a toroid envelope having one continuous uninterrupted wall, the wall having an exterior surface facing an exterior of the toroidal device, and an interior surface facing an interior of the toroidal device;

a hole passing through the toroidal device along a central axis of the toroidal device, the exterior surface having an inner part facing the hole and radially toward the central axis and an outer part facing away from the hole and radially away from the central axis;

the toroidal device having a top portion and a bottom portion respectively above and below the central axis, respective portions of the inner part of the exterior surface in the top portion and the inner part of the exterior surface in the bottom portion being adjacent and cooperating to form a channel:

the top portion comprising, within the interior;

i. a first top geared wheel;

ii. a second top geared wheel;

iii. a first top internal curved spiral (ICS) gear configured to engage the first top geared wheel;

iv. a second top ICS gear configured to engage the second top geared wheel;

v. a first top internal spur (IS) gear coupled to the first top ICS gear;

vi. a second top IS gear coupled to the second top ICS gear;

vii. a top DC motor having a first top spur gear at one end and a second top spur gear at another, opposite end, the first top spur gear configured to engage the first top IS gear and the second top spur gear configured to engage the second top IS gear;

the bottom portion comprising, within the interior:

i. a first bottom geared wheel;

ii. a second bottom geared wheel;

iii. a first bottom ICS gear configured to engage the first bottom geared wheel;

iv. a second bottom ICS gear configured to engage the second bottom geared wheel;

v. a first bottom IS gear coupled to the first bottom ICS gear;

vi. a second bottom IS gear coupled to the second bottom ICS gear;

vii. a bottom DC motor having a first bottom spur gear at one end and a second bottom spur gear at another, opposite end, the first bottom spur gear configured to engage the first bottom IS gear and the second bottom spur gear configured to engage the second bottom IS gear;

the first top ICS gear and the first bottom ICS gear are part of a single first ICS gear confined within the toroidal device and the first top IS gear and the first bottom IS gear are part of a single first IS gear within the toroidal device;

the second top ICS gear and the second bottom ICS gear are part of a single second ICS gear confined within the toroidal device and the second top IS gear and the second bottom IS gear are part of a single second IS gear within the toroidal device;

the top DC motor and the bottom DC motor are powered by at least one power source located within the toroidal device; and the top DC motor is configured to rotate the first top spur gear that engages the first top IS gear coupled to the first top ICS gear to cause the first top geared wheel to move rotationally in a first direction, and the top DC motor is configured to rotate the second top spur gear that engages the second top IS gear coupled to the second top ICS gear to cause the second top geared wheel to move rotationally in the first direction, resulting in a first inversion in the top portion such that at least a portion of the inner part of the exterior surface in the top portion becomes part of the outer part of the exterior surface in the top portion and at least a portion of the outer part of the exterior surface in the top portion becomes part of the inner part of the exterior surface in the top portion and, at the same time, the bottom DC motor is configured to rotate the first bottom spur gear that engages the first bottom IS gear coupled to the first bottom ICS gear to cause the first bottom geared wheel to move rotationally in a second direction, and the bottom DC motor is configured to rotate the second bottom spur gear that engages the second bottom IS gear coupled to the second bottom ICS gear to cause the second bottom geared wheel to move rotationally in the second direction, resulting in a second inversion in the bottom portion such that at least a portion of the inner part of the exterior surface in the bottom portion becomes part of the outer part of the exterior surface in the bottom portion and at least a portion of the outer part of the exterior surface in the bottom portion becomes part of the inner part of the exterior surface in the bottom portion, the first direction being opposite that of the second direction, the first and second inversions safely propelling the device without sliding of the outer part of the exterior surface in the top portion and the outer part of the exterior surface in the bottom portion against any contacted external wall and allowing low friction movement of the device.

20. The device as per claim 19, wherein the toroidal device is a toroidal balloon.

21. The device as per claim 19, wherein any one of the top DC motor or the bottom DC motor further comprises a set of planetary gears.

22. The device as per claim 19, wherein the device further comprises a chamber to hold or release any one of, or a combination of, the following: compressed gas, liquid or solid.

23. The device as per claim 19, further comprising a transmitter and an antenna configured to transmit a signal receivable by an external receiver to enable determination of a location of the device.

24. The device as per claim 19, wherein the device is configured to be positioned via a probe, a scope, or a catheter.

25. The device as per claim 19, wherein the inner part of the exterior surface in the top portion, the outer part of the exterior surface in the top portion, the inner part of the exterior surface in the bottom portion, and the outer part of the exterior surface in the bottom portion are made from nylon.

26. The device as per claim 19, wherein the device further comprises at least one light source and at least one camera disposed within the interior of the toroidal device in the top portion or the bottom portion.

27. The device as per claim 19, wherein the outer part of the exterior surface in the top portion or the outer part of the exterior surface in the bottom portion is coated with a coagulogenic substance, an antimicrobial agent, or a combination thereof.

* * * * *